United States Patent
Inouye et al.

(10) Patent No.: US 10,156,557 B2
(45) Date of Patent: Dec. 18, 2018

(54) CALCIUM-BINDING PHOTOPROTEIN

(71) Applicant: JNC CORPORATION, Tokyo (JP)

(72) Inventors: Satoshi Inouye, Kanagawa (JP); Yuiko Sahara, Kanagawa (JP)

(73) Assignee: JNC CORPORATION, Tokyo (JP)

( * ) Notice: Subject to any disclaimer, the term of this patent is extended or adjusted under 35 U.S.C. 154(b) by 54 days.

(21) Appl. No.: 14/291,543

(22) Filed: May 30, 2014

(65) Prior Publication Data

US 2014/0329250 A1    Nov. 6, 2014

Related U.S. Application Data

(62) Division of application No. 12/662,886, filed on May 10, 2010, now Pat. No. 8,772,452.

(30) Foreign Application Priority Data

May 14, 2009   (JP) .................. 2009-117972

(51) Int. Cl.
| | | |
|---|---|---|
| C12N 15/09 | (2006.01) | |
| C12N 15/12 | (2006.01) | |
| C12N 15/63 | (2006.01) | |
| G01N 33/20 | (2006.01) | |
| C07K 14/435 | (2006.01) | |

(52) U.S. Cl.
CPC ....... *G01N 33/20* (2013.01); *C07K 14/43595* (2013.01)

(58) Field of Classification Search
None
See application file for complete search history.

(56) References Cited

U.S. PATENT DOCUMENTS

| | | |
|---|---|---|
| 2005/0130262 A1 | 6/2005 | Lambolez et al. |
| 2007/0275377 A1 | 11/2007 | Golz et al. |
| 2009/0011460 A1* | 1/2009 | Inouye ............. C07K 14/43595 435/69.1 |

FOREIGN PATENT DOCUMENTS

| | | |
|---|---|---|
| GB | 2 440 273 | 1/2008 |
| GB | 2467429 | 8/2010 |
| JP | 2008-22848 | 2/2008 |
| WO | 2008/107104 | 9/2008 |

OTHER PUBLICATIONS

Rovelli et al. (1993) PNAS 90:8717-8721.*
S. Inouye et al., "Cloning and Sequence Analysis of cDNA for the Luminescent Protein Aequorin", Proc. Natl. Acad. Sci., vol. 82, pp. 3154-3158, May 1985.
J. F. Head et al., "The Crystal Structure of the Photoprotein Aequorin at 2.3A Resolution", Nature, vol. 405, pp. 372-376, May 18, 2000.
S. Inouye et al., "Cloning and Sequence Analysis of cDNA for the $Ca^{2+}$-Activated Photoprotein, Clytin", FEBS, vol. 315, No. 3, pp. 343-346, Jan. 1993.
S. Inouye, "Cloning, Expression, Purification and Characterization of an Isotype of Clytin, A Calcium-Binding Photoprotein from the Luminous Hydromedusa *Clytia gregarium*", J. Biochem., vol. 143, No. 5, pp. 711-717, 2008.
Search Report dated Sep. 7, 2010 for Patent Application No. GB 1007883.0.

* cited by examiner

*Primary Examiner* — Michael D Pak
(74) *Attorney, Agent, or Firm* — Wenderoth, Lind & Ponack, L.L.P.

(57) ABSTRACT

The invention provides calcium-binding photoproteins which can detect light emission with a higher sensitivity. The proteins of the invention comprising the amino acid sequence of SEQ ID NO: 2 can be used for the detection and measurement of calcium ions. The proteins of the invention are useful as reporter proteins, luminescent markers, etc. The polynucleotides of the invention are useful as reporter genes, etc.

11 Claims, 5 Drawing Sheets
Specification includes a Sequence Listing.

Fig. 2

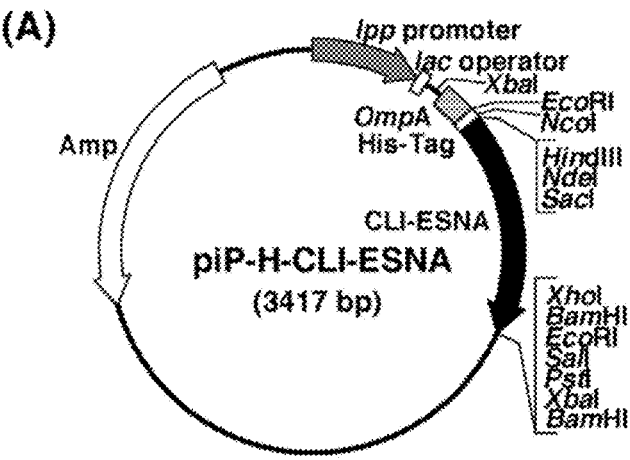

(B)

```
      M   K   K   T   A   I   A   I   A   V   A   L   A   G   F   A
     ATG AAA AAG ACA GCT ATC GCG ATT GCA GTG GCA CTG GCT GGT TTC GCT

T   V   A   Q   A   A   N   S   H   H   H   H   H   H   G   K
     ACC GTA GCG CAG GCC GCG AAT TCC CAC CAT CAC CAT CAC CAT GGT AAG
                              EcoRI              NcoI       HindIII
      L   H   M   E   L   R   P   N   F   D  ...  G   N   F   V   P   *
     CTT CAT ATG GAG CTG AGA CCC AAC TTC GAC ... GGC AAT TTT GTT CCT TAA
          NdeI    SacI                    Clytin-I-ESNA gene (3-189)

CTC GAG GGA TCC GAA TTC GTC GAC CTG CAG TCT AGA GGA TCC TGC TTG
       XhoI    BamHI   EcoRI    SalI    PstI    XbaI   BamHI

CGA AAA GCT CTA CGG TGG AGC TGT CCC CTA A...
```

CALCIUM-BINDING PHOTOPROTEIN

TECHNICAL FIELD

The present invention relates to calcium-binding photoproteins, genes encoding the same and use thereof.

BACKGROUND OF THE INVENTION

The calcium-binding photoproteins are present as a complex of an apoprotein and the peroxide of coelenterazine as a light-emitting substrate. The calcium-binding photoproteins emit a flash of light when bound to calcium ions.

Among the calcium-binding photoproteins including aequorin, obelin, clytin, mitrocomin, mineopsin and bervoin, aequorin is a well-characterized calcium-binding photoprotein, and its protein structure and the luminescence mechanism have been reported in detail (see, e.g., Inouye et al. (1985) Proc. Natl. Acad. Sci. USA 82, 3154-3158; and Head et al. (2000) Nature 405, 372-376). Due to its high sensitivity to calcium ions, aequorin is used to detect/quantify trace amounts of calcium ions, to measure changes in the concentration of intracellular calcium ions, and so on.

Clytin is a calcium-binding photoprotein isolated from the luminous jellyfish *Clytia gregoria* (see Inouye, S, and Tsuji, F. I. (1993) FEBS Lett, 315, 343-346; etc.). Clytin is present as a complex of apoclytin and the peroxide of coelenterazine as the light-emitting substrate. When bound to calcium ions, clytin emits a flash of light to produce coelenteramide, which is the oxidation product of coelenterazine, and carbon dioxide.

Herein, clytin can be classified into two groups, clytin-I and clytin-II (see, e.g., JPA 2008-22848; and Inouye, S (2008) J. Biochem. 143, 711-717). Of these two groups, clytin-H emits a flash of light when bound to calcium ions. The decay time of luminescence in clytin-II is a shorter than that of clytin-I.

DISCLOSURE OF INVENTION

Under the foregoing circumstances, there have been desired calcium-binding photoproteins which show a rapid decay pattern of luminescence and have a detectable luminescence with high sensitivity.

In order to solve the foregoing problems, the present inventors have made extensive investigations and as a result, have found that proteins comprising the amino acid sequence of SEQ ID NO: 2, etc. have the function capable of binding to the peroxide of coelenterazine or the peroxide of coelenterazine derivatives to form holoproteins that emit light by calcium ions. The inventors have also found that when the holoproteins described above are bound to calcium ions, a rapid decay pattern of luminescence is shown and the luminescence can be detected with a high sensitivity. Based on these findings, further investigations have been made and the present invention has come to be accomplished.

The present invention provides the following proteins, polynucleotides, recombinant vectors, transformants, and so on.

(1) A protein as defined by any one of (a) through (d) below:
(a) a protein consisting of the amino acid sequence of SEQ ID NO: 2;
(b) a protein consisting of the amino acid sequence of SEQ ID NO. 2, wherein the amino acids at positions 107, 110, 120, 140, 179 and 180 are aspartic acid, aspartic acid, glycine, proline, threonine and serine, respectively, and one to several amino acid(s) except for the amino acid(s) at the positions above are substituted with other amino acid(s), and having the binding ability to the peroxide of coelenterazine or the peroxide of a coelenterazine derivative to form a holoprotein that emits light by calcium ions;
(c) a protein comprising the amino acid sequence of SEQ ID NO: 2, and having the binding ability to the peroxide of coelenterazine or the peroxide of a coelenterazine derivative to form a holoprotein that emits light by calcium ions; and,
(d) a protein comprising the amino acid sequence of SEQ ID NO. 2, wherein the amino acids at positions 107, 110, 120, 140, 179 and 180 are aspartic acid; aspartic acid, glycine, proline, threonine and serine, respectively, and one to several amino acid(s) except for the amino acid(s) at the positions above are substituted with other amino acid(s), and having the binding ability to the peroxide of coelenterazine or the peroxide of a coelenterazine derivative to form a holoprotein that emits light by calcium ions.

(2) The protein according to (1) above, which is any one of (a) through (d) below:
(a) a protein consisting of the amino acid sequence of SEQ ID NO. 2;
(b) a protein consisting of the amino acid sequence of SEQ ID NO. 2, wherein the amino acids at positions 107, 110, 120, 140, 179 and 180 are aspartic acid, aspartic acid, glycine, proline, threonine and serine, respectively, and 1 to 16 amino acid(s) except for the amino acid(s) at the positions above are substituted with other amino acid(s), and having the binding ability to the peroxide of coelenterazine or the peroxide of a coelenterazine derivative to form a holoprotein that emits light by calcium ions;
(c) a protein comprising the amino acid sequence of SEQ ID NO: 2, and having the binding ability to the peroxide of coelenterazine or the peroxide of a coelenterazine derivative to form a holoprotein that emits light by calcium ions; and,
(d) a protein comprising the amino acid sequence of SEQ ID NO. 2, wherein the amino acids at positions 107, 110, 120, 140, 179 and 180 are aspartic acid, aspartic acid, glycine, proline, threonine and serine, respectively, and 1 to 16 amino acid(s) except for the amino acid(s) at the positions above are substituted with other amino acid(s), and having the binding ability to the peroxide of coelenterazine or the peroxide of a coelenterazine derivative to form a holoprotein that emits light by calcium ions.

(3) The protein according to (1) above, which is any one of (a) through (d) below:
(a) a protein consisting of the amino acid sequence of SEQ ID NO. 2;
(b) a protein consisting of the amino acid sequence of SEQ ID NO. 2, wherein the amino acids at positions 107, 110, 120, 140, 179 and 180 are aspartic acid, aspartic acid, glycine, proline, threonine and serine, respectively, and 1 to 6 amino acid(s) except for the amino acid(s) at the positions above are substituted with other amino acid(s), and having the binding ability to the peroxide of coelenterazine or the peroxide of a coelenterazine derivative to form a holoprotein that emits light by calcium ions;
(c) a protein comprising the amino acid sequence of SEQ ID NO: 2, and having the binding ability to the peroxide of coelenterazine or the peroxide of a coelenterazine derivative to form a holoprotein that emits light by calcium ions; and,
(d) a protein comprising the amino acid sequence of SEQ ID NO. 2, wherein the amino acids at positions 107, 110, 120, 140, 179 and 180 are aspartic acid, aspartic acid, glycine, proline, threonine and serine, respectively, and 1 to 6 amino acid(s) except for the amino acid(s) at the positions above are substituted with other amino acid(s), and having the binding ability to the peroxide of coelenterazine or the peroxide of a coelenterazine derivative to form a holoprotein that emits light by calcium ions.

(4) The protein according to (1) above which is (a) or (b) below
(a) a protein consisting of the amino acid sequence of SEQ ID NO. 2; or,
(b) a protein comprising the amino acid sequence of SEQ ID NO: 2, and having the binding ability to the peroxide of coelenterazine or the peroxide of a coelenterazine derivative to form a holoprotein that emits light by calcium ions.

(5) The protein according to any one of (1) through (4) above, further comprising a peptide sequence and/or secretory signal peptide for purification.

(6) A holoprotein comprising the protein according to any one of (1) through (5) above and the peroxide of coelenterazine or the peroxide of a coelenterazine derivative.

(7) A polynucleotide comprising a polynucleotide encoding the protein according to any one of (1) through (5) above (8) A recombinant vector comprising the polynucleotide according to (7) above.

(9) A transformant having inserted therein the recombinant vector according to (8) above.

(10) A method of producing the protein according to any one of (1) through (5) above, which comprises culturing the transformant of (9) above to produce the protein according to any one of (1) through (5) above.

(11) A kit comprising the protein according to any one of (1) through (5) above or the holoprotein according to (6) above.

(12) A kit comprising the polynucleotide of (7) above, the recombinant vector of (8) above or the transformant of (9) above.

(13) A method of detecting or quantifying a calcium ion, which comprises using the protein according to any one of (1) to (5) above or the holoprotein according to (6) above.

(14) A method of assaying the activity of a sequence associated with promoter control, which comprises using the polynucleotide of (7) above as a reporter gene.

(15) A method of measuring changes in intracellular calcium concentration, which comprises the step of expressing the polynucleotide of (7) above in a cell to form a photoprotein.

(16) A method of producing a fluorescent protein, which comprises reacting the protein according to any one of (1) through (5) above with coelenteramide or an analogue thereof in the presence or absence of a calcium ion or a divalent or trivalent ion that can be substituted for the calcium ion.

(17) The method according to (16) above, wherein the reaction is carried out in the presence of a reducing agent

(18) The method according to (16) or (17) above, wherein the reaction is carried out in the presence of a chelating agent to remove the calcium ion or the divalent or trivalent ion that can be substituted for the calcium ion.

The protein of the present invention can bind to the peroxide of coelenterazine or the peroxide of coelenterazine derivatives to form a holoprotein that emits light by calcium ions. The holoprotein produced from the protein in some embodiments of the invention provides a rapid decay pattern of luminescence and the luminescence can be detected with high sensitivity.

BRIEF DESCRIPTION OF DRAWINGS

FIG. 2 shows the construction of the expression vector piP-H-CLI-ESNA (EXAMPLE 3), wherein (A) shows a schematic representation of piP-H-CLI-ESNA and (B) shows a schematic representation of the nucleotide sequence of piP-H-CLI-ESNA.

Figure 1:
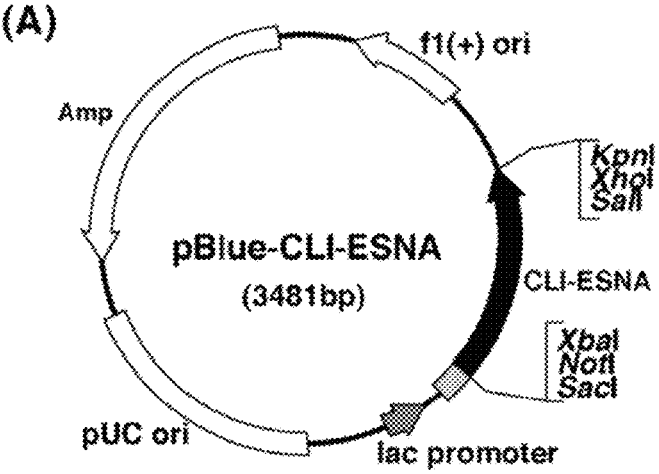
FIG. 1 shows the construction of the expression vector pBlue-CLI-ESNA (EXAMPLE 1), wherein (A) shows a schematic representation of pBlue-CLI-ESNA and (B) shows a schematic representation of the nucleotide sequence of pBlue-CLI-ESNA.

A: Bioluminescence emission spectrum of recombinant clytin-ESNA by the addition of a calcium solution
B: Fluorescence spectrum of the calcium-binding synthetic fluorescent protein prepared from recombinant apoclytin-ESNA and coelenteramide by excitation light at 335 nm
C: Fluorescence spectrum of the calcium-free synthetic fluorescent protein prepared from recombinant apoclytin-ESNA and coelenteramide by excitation light at 335 nm

BEST MODES FOR CARRYING OUT THE INVENTION

Hereinafter the present invention is described in detail with reference to the embodiments,
1. Protein of the Invention
The protein of the invention refers to a protein consisting of the amino acid sequence of SEQ ID NO: 2 and a protein which has substantially the same activity or function as the protein consisting of the amino acid sequence of SEQ ID NO: 2.

The term substantially the same activity or function is used to mean, for example, (i) the function that the protein above is capable of binding to the peroxide of coelenterazine or the peroxide of coelenterazine derivatives to form holoproteins, (ii) the function that the protein above is capable of binding to the peroxide of coelenterazine or the peroxide of coelenterazine derivatives to form holoproteins that emit light by calcium ions; (iii) a maximum intensity (Imax) of the luminescence generated by binding of the holoprotein described above to calcium ions is approximately ¼ or more, preferably approximately ⅓ or more, more preferably approximately ½ or more, and most preferably approximately 1/1.5, the maximum luminescence intensity (Imax) of the protein consisting of the amino acid sequence of SEQ ID NO: 2; and (iv) a half-life period ($T_{1/2}$, in seconds) of the luminescence generated by binding the holoproteins described above to calcium ions is 4 times or less, preferably approximately 3 times or less, more preferably approximately 2 times or less, and most preferably approximately 1.5 times or less, the half-life ($T_{1/2}$, in seconds) of the protein consisting of the amino acid sequence of SEQ ID NO: 2. The luminescence activity and luminescence pattern above may be determined by the methods described in, for example, Shimomura, O. et al., Biochem. J., 251, 405-410 (1988); Shimomura, O. et al., Biochem. J., 261, 913-920 (1989); etc.

Specifically, a luminescence reaction is initiated by adding a calcium solution to the holoprotein above, and the luminescence activity or pattern can be measured using a luminometer. Luminometers which may be used include commercially available instruments such as TD-4000 (manufactured by Labo Science) and Centro LB 960 (manufactured by Berthold).

As used herein, the term "a protein binds to the peroxide of coelenterazine or the peroxide of a coelenterazine derivative to form a holoprotein" means not only (1) that a protein binds to the peroxide of coelenterazine or the peroxide of a coelenterazine derivative to form a holoprotein but also (2) that a protein is brought in contact with the peroxide of coelenterazine or the peroxide of its derivative in the presence of oxygen to form a holoprotein (complex) containing the protein and the peroxide of coelenterazine or the peroxide of a coelenterazine derivative.

As used herein, the term coelenterazine derivative refers to a compound that binds to the protein of the invention to form a holoprotein capable of emitting light by calcium ions.

More specifically, the protein of the present invention includes, for example:

(a) a protein consisting of the amino acid sequence of SEQ ID NO. 2;

(b) a protein consisting of the amino acid sequence of SEQ ID NO. 2, wherein the amino acids at positions 107, 110, 120, 140, 179 and 180 are aspartic acid, aspartic acid, glycine, proline, threonine and serine, respectively, and one to several amino acid(s) except for the amino acid(s) at the positions above are substituted with other amino acid(s), and having substantially the same activity or function as the protein consisting of the amino acid sequence of SEQ ID NO. 2;

(c) a protein comprising the amino acid sequence of SEQ ID NO: 2 and having substantially the same activity or function as the protein consisting of the amino acid sequence of SEQ ID NO. 2;

(d) a protein comprising the amino acid sequence of SEQ ID NO. 2, wherein the amino acids at positions 107, 110, 120, 140, 179 and 180 are aspartic acid, aspartic acid, glycine, proline, threonine and serine, respectively, and one to several amino acid(s) except for the amino acid(s) at the positions above are substituted with other amino acid(s), and having substantially the same activity or function as the protein consisting of the amino acid sequence of SEQ ID NO: 2; and the like.

The protein comprising the amino acid sequence of SEQ ID NO: 2 includes, for example, (a) a protein consisting of the amino acid sequence of SEQ ID NO: 2, 4 or 6;

(b) a protein comprising the amino acid sequence of SEQ ID NO: 2, 4 or 6; and the like.

The protein comprising the amino acid sequence of SEQ ID NO. 2, wherein the amino acids at positions 107, 110, 120, 140, 179 and 180 are aspartic acid, aspartic acid, glycine, praline, threonine and serine, respectively, and one to several amino acid(s) except for the amino acid(s) at the positions above are substituted with other amino acid(s) includes:

(a) a protein consisting of the amino acid sequence of SEQ ID NO. 2, wherein the amino acids at positions 107, 110, 120, 140, 179 and 180 are aspartic acid, aspartic acid, glycine, proline, threonine and serine, respectively, and one to several amino acid(s) except for the amino acid(s) at the positions above are substituted with other amino acid(s);

(b) a protein comprising the amino acid sequence of SEQ ID NO. 2, wherein the amino acids at positions 107, 110, 120, 140, 179 and 180 are aspartic acid, aspartic acid, glycine, praline, threonine and serine, respectively, and one to several amino acid(s) except for the amino acid(s) at the positions above are substituted with other amino acid(s); and the like.

The term "one to several amino acid(s) are substituted" described above is used to mean that one or more amino acid residues are substituted at any one or more positions in the same amino acid sequence.

Hereinafter, examples of mutually substitutable amino acid residues are en are given below. Amino acid residues in the same group can be mutually substituted.

Group A: leucine, isoleucine, norleucine, valine, norvaline, alanine, 2-aminobutanoic acid, methionine, o-methylserine, t-butylglycine, t-butylalanine and cyclohexylalanine;

Group B: aspartic acid, glutamic acid, isoaspartic acid, isoglutamic acid, 2-aminoadipic acid and 2-aminosuberic acid;

Group C: asparagine and glutamine;

Group D: lysine, arginine, ornithine, 2,4-diaminobutanoic acid and 2,3-diaminopropionic acid;

Group E: proline, 3-hydroxyproline and 4-hydroxyproline;

Group F: serine, threonine and homoserine, and,

Group G: phenylalanine and tyrosine.

As used herein, the range of "one to several" in "the amino acid sequence in which one to several amino acid(s) are substituted with other amino acid(s)" refers to, for example, 1 to 16, 1 to 10, 1 to 9, 1 to 8, 1 to 7, 1 to 6 (1 to several), 1 to 5, 1 to 4, 1 to 3, 1 or 2, or 1. A smaller number of the substituted amino acids is generally more preferred. Such proteins may be obtained by using a site-specific mutagenesis technique described in, e.g., Sambrook J. et al., Molecular Cloning: A Laboratory Manual, Third Edition, Cold Spring Harbor Laboratory Press (2001); Ausbel F. M. et al, Current Protocols in Molecular Biology, Supplement 1-38, John Wiley and Sons (1987-1997); Nuc. Acids. Res., 10, 6487 (1982); Proc. Natl. Acad. Sci. USA, 79, 6409 (1982); Gene, 34, 315 (1985); Nuc. Acids. Res., 13, 4431 (1985), Proc. Natl. Acad. Sci. USA, 82, 488 (1985); etc.

The positions of amino acids substituted in the amino acid sequence of SEQ ID NO: 2 are not particularly limited as far as they are positions other than the positions 107, 110, 120, 140, 179 and 180, and are one to several positions selected from positions 1 to 12, positions 47 to 103, and the like, preferably one to several positions selected from the group consisting of positions 4, 5, 6, 8, 11, 47, 49, 52, 53, 55, 56, 59, 60, 61, 62, 64, 67, 68, 59, 71, 72, 74, 75, 76, 77, 78, 79, 81, 82, 83, 84, 86, 87, 88, 91, 92, 93, 95, 96, 97, 98, 99, 101, 102 and 103.

In a particularly preferred embodiment of the present invention, the protein is (a) a protein consisting of the amino acid sequence of SEQ ID NO: 2, (b) a protein comprising the amino acid sequence of SEQ ID NO: 2, and having the binding ability to the peroxide of coelenterazine or the peroxide of a coelenterazine derivative to form a holoprotein that emits light by calcium ions, etc.

The protein of the invention may include an additional peptide sequence at the N terminus and/or the C terminus, preferably at the N terminus. The additional peptide sequence includes, for example, at least one peptide sequence selected from the group consisting of a peptide sequence for purification, a secretory signal peptide sequence and an epitope sequence recognizable by an antibody. The peptide sequence which may be additionally used is preferably a peptide sequence for purification and/or a secretory signal peptide sequence. The peptide sequence for purification which may be used includes a peptide sequence employed in the technical field of the invention. Examples of the peptide sequence for purification include a histidine tag sequence having a consecutive amino acid sequence of at least four, preferably at least six, histidine residues, the amino acid sequence of the glutathione-binding domain in glutathione S-transferase and the amino acid sequence of protein A. The term secretory signal peptide refers to a peptide region which plays the role of transporting the protein or polypeptide bound to the secretory signal peptide across the cell membrane. The amino acid sequences of such secretory signal peptides and nucleotide sequences encoding these peptides are well known and reported in the relevant art (cf, e.g., von Heijine G (1988) Biochim. Biophys. Acta 947:307-333, von Heijine G (1990) J. Membr. Biol. 115: 195-201, etc). More specifically, secretory signal peptides include, for example, the secretory signal peptide from the outer membrane protein A from *E. coli* (OmpA) (Ghrayeb, J. et al., EMBO J. (1984), 3, 2437-2442) and the secretory signal peptide from cholera toxin obtained from *Vibrio cholerae*.

Methods for producing the protein of the invention are not particularly limited. The protein of the invention may be a protein synthesized by chemicasl synthesis, or a recombinant protein produced by a genetic engineering technique. In chemically synthesizing the protein of the invention, the protein may be synthesized by, for example, the Fmoc (fluorenylmethyloxycarbonyl) process, the tBoc (t-butyloxycarbonyl) process, etc. In addition, the peptide may be chemically synthesized using peptide synthesizers manufactured by Advanced ChemTech, PerkinElmer, Pharmacia, Protein Technology Instrument, Synthecell-Vega, PerSeptive, Shimadzu Corporation, etc. In producing the protein of the invention by a genetic engineering technique, the protein may be produced in a conventional manner by a genetic recombination technique. More specifically, the protein of the present invention may be produced by introducing a polynucleotide (e.g., DNA) encoding the protein of the invention into a suitable expression system. The polynucleotide encoding the protein of the invention and expression of the protein of the invention in an expression system are described later.

The protein of the invention is brought in contact with luminescent substrate coelenterazine or a derivative thereof (e.g., h-coelenterazine, e-coelenterazine, cl-coelenterazine, ch-coelenterazine, hcp-coelenterazine, etc.) in the presence of oxygen, whereby the holoprotein composed of the protein of the invention and the peroxide of coelenterazine or the peroxide of a coelenterazine derivative can be obtained. Hereinafter the "coelenterazine or a derivative thereof" is sometimes briefly referred to as "coelenterazine." As used herein, the holoprotein composed of the protein of the invention and the peroxide of coelenterazine or the peroxide of a coelenterazine derivative is sometimes referred to as "the holoprotein of the invention." Herein, the "holoprotein (photoprotein) of the invention" is used to mean a complex (holoprotein) comprising the protein of the invention (apoprotein) and the peroxide of coelenterazine or the peroxide of a coelenterazine derivative, Examples of the holoprotein of the invention include a holoprotein composed of the protein of the invention and the peroxide of coelenterazine, a holoprotein composed of the protein of the invention and the peroxide of a coelenterazine derivative, and the like. Examples of the holoprotein composed of the protein of the invention and the peroxide of a coelenterazine derivative include a holoprotein composed of the protein of the invention and the peroxide of h-coelenterazine, a holoprotein composed of the protein of the invention and the peroxide of e-coelenterazine, a holoprotein composed of the protein of the invention and the peroxide of n-coelenterazine, a holoprotein composed of the protein of the invention and the peroxide of ch-coelenterazine, a holoprotein composed of the protein of the invention and the peroxide of hcp-coelenterazine, and the like. The holoprotein of the invention can be produced from the protein of the invention and the coelenterazine in the same manner as with known calcium-binding photoproteins (e.g., aequorin, etc.). More specifically, the holoprotein of the invention can be produced by methods described in, for example, Shimomura, O. et al., (1988) Biochem. J., 251, 405-410; Shimomura, O. et al., Biochem, J. (1989) 261, 913-920, etc. The holoprotein of the invention exists in the presence of oxygen, in the state of a complex of the protein of the invention and the peroxide of coelenterazine which is formed from coelenterazine and molecular oxygen. When calcium ions bind to this complex, a flash of light is emitted to form coelenteramide as the oxide of coelenterazine and carbon dioxide. This complex (holoprotein of the invention) is sometimes referred to as the "photoprotein of the invention,"

2. Polynucleotide of the Invention

The present invention further provides a polynucleotide encoding the protein of the invention described above. The polynucleotide of the invention may be any polynucleotide so long as it has a nucleotide sequence encoding the protein of the invention, preferably a DNA. Examples of the DNA include genomic DNA, genomic DNA library, cDNA derived from cells or tissues, cDNA library derived from cells or tissues, synthetic DNA, etc. The vectors used in these libraries are not particularly limited and may be any of bacteriophages, plasmids, cosmids and phagemids. The polynucleotide may also be amplified directly by a reverse transcription polymerase chain reaction (hereinafter abbreviated as RT-PCR) using total RNA or a mRNA fraction prepared from the cells or tissues described above.

The polynucleotide of the present invention includes:

(a) a polynucleotide comprising a polynucleotide consisting of the nucleotide sequence of SEQ ID NO: 1;

(b) a polynucleotide comprising a polynucleotide encoding the protein consisting of the amino acid sequence of SEQ ID NO: 2;

(c) a polynucleotide comprising a polynucleotide encoding a protein consisting of the amino acid sequence of SEQ ID NO. 2, wherein the amino acids at positions 107, 110, 120, 140, 179 and 180 are aspartic acid, aspartic acid, glycine, proline, threonine and serine, respectively, and one to several amino acid(s) except for the amino acid(s) at the positions above are substituted with other amino acid(s), and having substantially the same activity or function as the protein consisting of the amino acid sequence of SEQ ID NO: 2;

(e) a polynucleotide comprising a polynucleotide encoding a protein comprising the amino acid sequence of SEQ ID NO: 2, and having substantially the same activity or function as the protein consisting of the amino acid sequence of SEQ ID NO: 2;

(f) a polynucleotide comprising a polynucleotide encoding a protein comprising the amino acid sequence of SEQ ID NO. 2, wherein the amino acids at positions 107, 110, 120, 140, 179 and 180 are aspanic acid, aspartic acid, glycine, proline, threonine and serine, respectively, and one to several amino acid(s) except for the amino acid(s) at the positions above are substituted with other amino acid(s), and having substantially the same activity or function as the protein consisting of the amino acid sequence of SEQ ID NO: 2; and the like.

Examples of the polynucleotide comprising a polynucleotide consisting of the nucleotide sequence of SEQ ID NO: 1 include:

(a) a polynucleotide consisting of the nucleotide sequence of SEQ ID NO: 1, 3 or 5;

(b) a polynucleotide comprising a polynucleotide consisting of the nucleotide sequence of SEQ ID NO: 1, 3 or 5; and the like.

The substantially the same activity or function is as defined hereinabove

The term "amino acid sequence in which one to several amino acid(s) are substituted" is also as defined hereinabove.

The polynucleotide encoding a protein having, with respect to a given amino acid sequence, one to several amino acids being substituted can be obtained using a site-specific mutagenesis technique (see, for example, Gotoh, T. et al., Gene, 152, 271-275 (1995); Zoller, Mi., and Smith, M., Methods Enzymol., 100, 468-500 (1983); Kramer, \V. et al., Nucleic Acids Res., 12, 9441-9456 (1984); Kramer W, and Fritz H. J., Methods. Enzymol. 154, 350-367 (1987); Kunkel, T. A., Proc. Natl. Acad. Sci. USA., 82, 488-492 (1985), Kunkel, Methods Enzymol., 85, 2763-2766 (1988); etc.), and methods using amber mutation (see, for example, the gapped duplex method described in Nucleic Acids Res., 12, 9441-9456 (1984), etc.).

Alternatively, a mutation can be introduced into the polynucleotide by PCR using a set of primers bearing on the respective 5' ends a sequence in which the target mutation (deletion, addition, substitution and/or insertion) is introduced (see, for example. Ho, S, N. et al., Gene, 77, 51 (1989), etc.)

Furthermore, a polynucleotide encoding a partial fragment of protein, which is one type of deletion mutants, can be obtained by PCR using as the primers an oligonucleotide having a sequence that matches the nucleotide sequence at the 5' end of the region encoding the target partial fragment in a polynucleotide encoding the protein and an oligonucleotide having a sequence complementary to the nucleotide sequence at the 3' end, and using the polynucleotide encoding the protein as a template.

Preferably, the polynucleotide of the present invention is, for example, a polynucleotide comprising a polynucleotide consisting of the nucleotide sequence of SEQ ID NO: 1, a polynucleotide comprising a polynucleotide encoding a protein consisting of the amino acid sequence of SEQ ID NO: 2, a polynucleotide comprising a polynucleotide encoding a protein comprising the amino acid sequence of SEQ ID NO: 2 and having substantially the same activity or function as the protein consisting of the amino acid sequence of SEQ ID NO: 2, and the like.

The polynucleotide of the present invention may further contain a polynucleotide encoding an additional peptide sequence at the 5' end and/or 3' end, preferably at the 5' end. The polynucleotide encoding the additional peptide sequence may include, for example, at least one peptide sequence selected from the group consisting of a peptide sequence for purification, a secretory signal peptide sequence, etc. The peptide sequence for purification which may be used includes a peptide sequence employed in the technical field of the invention. The peptide sequence for purification includes those described above. The polynucleotide encoding a secretory signal peptide which may be used includes a polynucleotide comprising a nucleic acid sequence encoding a secretory signal peptide known in the art. The secretory signal peptide includes those described above.

3. Recombinant Vector and Transformant of the Invention

The present invention further provides a recombinant vector comprising the polynucleotide of the invention described above and a transformant.

(1) Construction of Recombinant Vector

The recombinant vector of the present invention can be obtained by ligating (inserting) the polynucleotide (DNA) of the invention into a suitable vector. More specifically, the recombinant vector can be obtained by cleaving a purified form of the polynucleotide (DNA) with a suitable restriction enzyme and inserting the cleavage product into a restriction enzyme site or multicloning site on a suitable vector, thereby ligating the polynucleotide to the vector. The vector for inserting the polynucleotide of the invention is not particularly limited, as far as the vector is capable of replication in a host. Vectors which may be used include plasmids, bacteriophages, animal viruses, etc. Examples of such plasmids include plasmids from E. coli (e.g., pBR322, pBR325, pUC118, pUC119, etc.), plasmids from Bacillus subtilis (e.g., pUB110, pTP5, etc.), and plasmids from yeast (e.g., YEp13, YEp24, YCp50, etc.). An example of the bacteriophage is a λ phage. Examples of the animal viruses include retroviruses, vaccinia viruses and insect viruses (e.g., baculoviruses, etc.).

The polynucleotide of the present invention is generally ligated downstream from the promoter of a suitable vector in such a manner that it can be expressed. Where the host used for transformation is an animal cell, preferred examples of the promoter used include a promoter from SV40, a retrovirus promoter, a metallothionein promoter, a heat shock promoter, a cytomegalovirus promoter, a SRa promoter, etc. Where the host is a bacterium belonging to the genus Escherichia, preferred examples of the promoter include a Trp promoter, T7 promoter, lac promoter, recA promoter, λPL promoter and 1 pp promoter, etc. Where the host is a bacterium belonging to the Bacillus, preferred examples of the promoter include a SPO1 promoter, SPO2 promoter and the penP promoter. If the host is a yeast, preferred promoters include the PHO5 promoter, the PGK promoter, the GAP promoter, the ADH1 promoter and GAL promoter, etc. Where the host is an insect cell, preferred examples of the promoter include a polyhedrin promoter and P10 promoter, etc.

In addition to those described above, the recombinant vector of the present invention which can be used include those containing, if desired, an enhancer, a splicing signal, a poly(A) addition signal, a ribosome binding sequence (SD sequence), a selective marker and the like. Examples of the selective marker include a dihydrofolate reductase gene, ampicillin resistance gene and neomycin resistance gene.

(2) Preparation of Transformant

The transformant can be prepared by introducing the recombinant vector comprising the polynucleotide of the invention thus obtained (i.e., the polynucleotide encoding the protein of the invention) into a suitable host. The host is not particularly limited, so long as it is capable of expressing the polynucleotide (DNA) of the invention. Examples of the host include bacteria belonging to the genera Escherichia, Bacillus, Pseudomonas and Rhizobium, yeasts, animal cells or insect cells, etc. Bacteria of the genus Escherichia include Escherichia coli, etc. Bacteria of the genus Bacillus include Bacillus subtilis, etc. Bacteria of the genus Pseudomonas include Pseudomonas putida, etc. Bacteria of the genus Rhizobium include R. meliloti, etc. Yeasts include Saccha-

*romyces cerevisiae, Schizosaccharomyces pombe*, etc. Animal cells include COS cells, CHO cells, etc. Insect cells include Sf9, Sf21, etc.

Introduction of the recombinant vector into the host and transformation thereby can be performed by various methods generally used in the art. Examples of suitable methods for introducing the recombinant vector into host cells include the calcium phosphate method (Virology, 52, 456-457 (1973)), lipofection (Proc. Natl. Acad. Sci. USA, 84, 7413 (1987)), electroporation (EMBO J., 1, 841-845 (1982)), etc. Examples of methods for transforming bacteria of the genus *Escherichia* include the methods described in Proc. Natl. Acad. Sci. USA, 69, 2110 (1972), Gene, 17, 107 (1982), etc. Methods for transforming bacteria of the genus *Bacillus* include the methods described in Molecular & General Genetics, 168, 111 (1979), etc. Methods for transforming yeasts include the methods described in Proc. Natl. Acad. Sci. USA, 75, 1929 (1978), etc. Methods for transforming animal cells include the methods described in Virology, 52, 456 (1973), etc. Methods for transforming insect cells include the methods described in Bio/Technology, 6, 47-55 (1988), etc. Thus, the transformant prepared by transformation with the recombinant vector comprising the polynucleotide encoding the protein of the invention (i.e., the polynucleotide of the invention) can be obtained.

4. Production of Protein of the Invention

The present invention further provides a method of producing the protein of the invention, which comprises the step of culturing the transformant described above to produce the protein of the invention. The protein of the invention can be produced by culturing the transformant above under conditions where the polynucleotide (DNA) encoding the protein of the invention can be expressed, to produce and accumulate the protein of the invention, and isolating and purifying the protein.

(Incubation of Transformant)

The transformant of the invention can be cultured in a conventional manner used for incubation of hosts. By the incubation, the protein of the invention is produced using the transformant and accumulated within the transformant or in the culture broth.

The medium for culturing the transformant, which is used to incubate bacteria of the genus *Escherichia* or *Bacillus* as the host, may be any of a natural medium or a synthetic medium, so long as it is a medium containing carbon sources, nitrogen sources, inorganic salts and other nutrients essential for growth of the transformant where the transformant can be efficiently grown. Examples of the carbon sources which can be used include carbohydrates such as glucose, fructose, sucrose, starch, etc.; organic acids such as acetic acid, propionic acid, etc.; and alcohols such as ethanol, propanol, etc. Examples of the nitrogen sources which can be used include ammonia, ammonium salts of inorganic or organic acids, such as ammonium chloride, ammonium sulfate, ammonium acetate, ammonium phosphate, etc., other nitrogen-containing compounds, and further include peptone, meat extract, corn steep liquor, etc. Examples of the inorganic salts that can be used include potassium (I) phosphate, potassium (II) phosphate, magnesium phosphate, magnesium sulfate, sodium chloride, ferrous sulfate, manganese sulfate, copper sulfate, calcium carbonate, etc. If necessary, antibiotics such as ampicillin or tetracycline may be added to the medium during culturing. Where the transformant transformed by an expression vector using an inducible promoter as the promoter is cultured, an inducer may also be added to the medium if necessary. For example, isopropyl-β-D-thiogalactopyranoside (IPTG), etc. may be added to the medium when a transformant transformed by an expression vector using a Lac promoter is cultured, and when a transformant transformed by an expression vector using a trp promoter is cultured, indoleacrylic acid (IAA), etc. may be added to the medium.

When the host is a bacterium of the genus *Escherichia*, incubation is performed generally at approximately 15 to 43° C. for approximately 3 to 24 hours. Aeration or stirring may be applied depending upon necessity. When the host is a bacterium of the genus *Bacillus*, incubation is carried out generally at approximately 30 to 40° C. for approximately 6 to 24 hours. Aeration or stirring may be applied depending upon necessity.

Media for culturing the transformant when the host is yeast include Burkholder's minimal medium (Proc. Natl. Acad, Sci. USA, 77, 4505 (1980)), a SD medium containing 0.5% (w/v) casamino acids (Proc. Natl. Acad. Sci. USA, 81, 5330 (1984)), etc. The pH of the medium is preferably adjusted to approximately 5 to 8. Culture is generally carried out at approximately 20 to 35° C. for approximately 24 to 72 hours. Aeration or stirring may be applied, depending upon necessity.

Media for culturing the transformant when the host is an animal cell include MEM medium containing approximately 5 to 20% (v/v) fetal calf serum (Science, 122, 501 (1952)), DMEM medium (Virology, 8, 396 (1959)), etc. The pH of the medium is preferably adjusted to approximately 6 to 8. Culture is generally carried out at approximately 30 to 40° C. for approximately 15 to 60 hours. Aeration or stirring may be applied, depending upon necessity.

Media for culturing the transformant when the host is an insect cell include Grace's insect medium (Nature, 195, 788 (1962)) suitably supplemented with additives such as 10% (v/v) immobilized bovine serum. The pH of the medium is preferably adjusted to approximately 6.2 to 6.4. Culture is generally carried out at approximately 27° C. for approximately 3 to 5 days, Aeration or stirring may be applied, depending upon necessity.

(Isolation and Purification of Protein of the Invention)

The protein of the invention can be obtained by isolating and purifying the protein of the invention from the culture above. As used herein, the culture refers to any one of a culture broth, cultured bacterial cells or cultured cells, and the homogenates of cultured bacterial cells or cultured cells. The isolation and purification of the protein of the invention can be performed in a conventional manner.

Specifically, when the protein of the invention is accumulated within cultured bacterial cells or within cultured cells, after the completion of cultivation, the bacterial cells or cells are disrupted in a conventional manner (e.g., ultrasound, lysozymes, freezing and thawing) and a crude extract of the protein of the present invention can be obtained in a conventional manner (e.g., centrifugation, filtration, etc.). When the protein of the invention is accumulated in the periplasmic space, after the completion of cultivation, an extract containing the target protein can be obtained in a conventional manner (e.g., osmotic shock, etc.). When the protein of the invention is accumulated in the culture broth, after the completion of cultivation, the bacteria or cells are separated from the culture supernatant in a conventional manner centrifiigation, filtration, etc.), whereby the culture supernatant containing the protein of the invention can be obtained.

The protein of the present invention in the extract or culture supernatant thus obtained can be purified by a conventional method of separation and purification. Examples of the separation and purification methods include ammonium sulfate precipitation, gel filtration chromatography, ion-exchange chromatography, affinity chromatography, reversed phase high performance liquid chromatography, dialysis, ultrafiltration, etc., which may be used solely or in a suitable combination. Where the protein of the invention contains the above-described peptide sequence for purification, it is preferred to use the same for purification. Specifically, where the protein of the invention contains a histidine-tagged sequence, nickel chelate affinity chromatography can be used, in the protein of the invention which contains the glutathione-binding domain of S-transferase, affinity chromatography using a glutathione-binding gel can be used; and, in the protein of the invention which contains the amino acid sequence of Protein A, antibody affinity chromatography can be used.

The holoprotein (photoprotein) of the invention which emits light dependently on the calcium ion concentration can be prepared by incubation of the purified apoprotein of the invention together with the luminescent substrate coelenterazine or its derivative at a low temperature in the presence of a reducing agent (e.g., mercaptoethanol, dithiothreitol, etc.) and oxygen, 5. Uses of Protein of the Invention
(Detection and Quantification of Calcium Ions)

As described above, the protein (apoprotein) of the invention is a protein which can be produced by forming a non-covalent bond with the peroxide of coelenterazine or the peroxide of a coelenterazine derivative, which is formed from coelenterazine or its derivative and molecular oxygen, and can form a holoprotein (photoprotein) which emits light by calcium ions. The protein of the invention and the holoprotein of the invention can be used for detecting or quantifying calcium ions.

When the protein of the invention is used to detect or quantify calcium ions, the holoprotein composed of the protein (apoprotein) of the invention and the peroxide of coelenterazine or the peroxide of a coelenterazine derivative is used. The holoprotein described above can be produced by the method described above. The detection or quantification of calcium ions can be performed by adding a sample solution directly to a solution of the holoprotein and measuring the luminescence generated. The detection or quantification of calcium ions can also be performed by adding a solution of the holoprotein to a sample solution and measuring the luminescence generated. Alternatively, prior to the addition in the measurement system for detection or quantification of calcium ions, an aqueous solution of the protein (apoprotein) of the invention is previously brought in contact with coelenterazine or its derivative (e.g., h-coelenterazine, e-coelenterazine, cl-coelenterazine, ch-coelenterazine, hep-coelenterazine, etc.) and the holoprotein thus formed may be used. Furthermore, the protein (apoprotein) of the invention may also be brought in contact with coelenterazine or its derivative in the measurement system to form a holoprotein composed of the protein of the invention and the peroxide of coelenterazine or the peroxide of a coelenterazine derivative. The holoprotein thus formed is a complex (photoprotein) of the protein (apoprotein) of the invention and the peroxide of coelenterazine or the peroxide of a coelenterazine derivative; the aforesaid complex (i.e., the holoprotein of the invention) emits light dependently on the calcium ion concentration. Accordingly, the protein (apoprotein) of the invention or the holoprotein of the invention can be used to detect calcium ions. Specifically, the calcium ions can be detected by adding a sample solution directly to a solution of the holoprotein and measuring the luminescence generated, as described above.

Alternatively, the calcium ions can be detected by adding a solution of the holoprotein to a sample solution and then measuring the luminescence generated.

The detection or quantification of calcium ions can be performed by measuring the luminescence of the holoprotein of the invention by calcium ions using a luminometer. Luminometers which can be used include commercially available instruments such as Centro LB 960 (manufactured by Berthold), etc. The calcium ion concentration can be quantitatively determined by preparing a luminescence standard curve for known calcium ion concentrations using the holoprotein.

The protein of the invention may also be used to detect changes in the concentration of intracellular calcium ions under physiological conditions, by constructing a holoprotein composed of the protein of the invention and the peroxide of coelenterazine or the peroxide of a coelenterazine derivative, and directly introducing the holoprotein into the cell by means of microinjection, etc.

In addition to the introduction into a cell by means of microinjection, etc., the protein of the invention may be formed intracellularly by intracellularly expressing an apoprotein gene (a polynucleotide encoding the protein of the invention). The holoprotein may also be formed by adding coelenterazine or its derivative to the protein (apoprotein) of the invention thus formed from outside the cell.

Using the holoprotein of the invention thus introduced into or formed within the cell, changes in the concentration of intracellular calcium ions in response to external stimuli (e.g., stimuli with a drug which is associated with a receptor) can also be measured.

(Use as Reporter Protein)

The protein of the invention can be used also as a reporter protein to assay the transcription activity of a promoter or the like. The polynucleotide encoding the protein of the invention (i.e., the polynucleotide of the invention) is fused to a target promoter or some other expression control sequence (e.g., an enhancer, etc.) to construct a vector. The resulting vector is introduced into a host cell and the luminescence generated from the protein of the invention (i.e., the luminescence by the holoprotein of the invention) is detected. Thus, the activity of the target promoter or some other expression control sequence can be assayed.

As described above, the polynucleotide of the invention can be used as a reporter gene (Use as Marker for Detection by Luminescence)

The protein of the invention can be used as a marker for detection by luminescence. The detection marker of the invention is available for the detection of a target substance in, for example, an immunoassay or hybridization assay. The holoprotein of the invention can be used by binding the same to a target protein or a target nuclei acid in a conventional manner such as chemical modifications. Such detection markers can be used for the detection in a conventional manner. The detection marker of the invention can also be used to determine the distribution of a target protein by expressing the marker as a fusion protein to the target protein and inserting the fusion protein into a cell by means of microinjection, etc. The distribution of a target protein described above can be determined by a method for detection such as luminescence imaging. The protein of the invention can also be used after expression of the protein in a cell, in addition to the insertion into a cell by means of microinjection, etc.

(Material for Amusement Product)

The complex composed of the protein of the invention and the peroxide of coelenterazine or the peroxide of a coelenterazine derivative (the complex is the holoprotein of the invention) emits light merely by binding to a trace amount of calcium ions. The luminescence intensity of the complex (the holoprotein of the invention) above is at least five times greater than that of the known photoprotein clytin-I. Therefore, the protein of the invention, the holoprotein of the invention and the like can be suitably used as a luminescent substrate in materials for amusement products. Examples of amusement products include luminescent bubble soap, luminescent ice, luminescent candies and luminescent paints. The amusement products of the invention can be prepared in a conventional manner.

6. Kit of the Invention

The present invention further provides a kit comprising any of the protein of the invention, the holoproteins of the invention, the polynucleotide of the invention, the recombinant vector of the invention and the transformant of the invention. The kit of the invention may additionally contain coelenterazine or a derivative thereof. The kit of the invention can be prepared according to conventional methods using conventional materials. The kit of the invention may also contain sample tubes, plates, instructions for the user, solutions, buffers, reagents, and either samples suitable for standardization or control samples.

The kit of the present invention can be used for the detection or quantification of calcium ions described above, the measurement using a reporter protein or a reporter gene, as a fluorescent marker, or the like.

7. Fluorescent Protein 7.1 Method of Producing Fluorescent Protein

The fluorescent protein produced by the method of producing the fluorescent protein of the invention is a complex in which coelenteramide or its analog is coordinated to the protein of the invention. The fluorescent protein of the invention can emit fluorescence under the excitation of light. In some embodiments, the fluorescent protein of the invention has both bioluminescence and fluorescence spectrum, wherein, for example, the fluorescence maximum wavelength is shifted toward a longer wavelength region than the luminescence maximum wavelength.

In the present invention, the fluorescent protein is produced from coelenteramide or its analog by the following procedures. In more detail, the fluorescent protein is produced by reacting the protein of the invention with coelenteramide or its analog in the presence or absence of calcium ions or divalent or trivalent ions that can be substituted for the calcium ions.

In the present invention, coelenteramide or its analog which is used to produce the fluorescent protein includes the compounds described in the pamphlet of WO 2005/014633, page 6, line 15 to page 7, line 23, the compounds represented by general formula (1) below, and the like.

Compounds represented by the formula below.

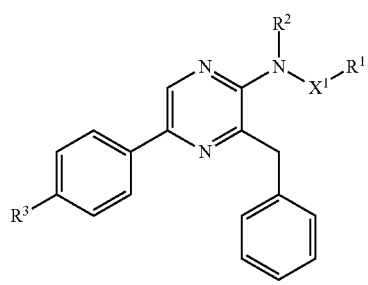

(1)

(wherein $R^1$ is a substituted or unsubstituted aryl, a substituted or unsubstituted arylalkyl, a linear or branched alkyl which may optionally be substituted with an alicyclic group, an alicyclic group or a heterocyclic group;

$R^2$ is hydrogen or $-(SO_2)R^4$;

$R^3$ is hydrogen, hydroxy group, methoxy or acetoxy; and, $R^4$ is substituted or unsubstituted aryl, a substituted or unsubstituted arylalkyl or a linear or branched alkyl which may optionally be substituted with an alicyclic group; and, $X^1$ is $-C(=S)-$ or $-SO_2-$).

Herein, in general formula (1), it is preferred that $R^1$ is phenyl, p-methylphenyl, p-hydroxyphenyl, p-methoxyphenyl, p-acetoxyphenyl, p-nitrophenyl, benzyl, α-hydroxybenzyl, 4-methylbenzyl, 4-hydroxybenzyl, 4-methoxybenzyl, 4-acetoxybenzyl, 4-nitrobenzyl, phenylethyl, methyl, ethyl, propyl, 2-methylpropyl, 2-methylpropanyl, cyclohexylmethyl, cyclohexylethyl, adamantylmethyl, cyclopentylmethyl, cyclohexyl or thiophen-2-yl.

Further in general formula (1), it is preferred that $R^2$ is hydrogen, benzenesulfonyl, p-toluenesulfonyl, 4-hydroxyphenylsulfonyl, 4-methoxyphenylsulfonyl, 4-acetoxyphenylsulfonyl, 4-nitrophenylsulfonyl, benzylsulfonyl, α-hydroxybenzylsulfonyl, 4-methylbenzylsulfonyl, 4-hydroxybenzylsulfonyl, 4-methoxybenzylsulfonyl, 4-acetoxybenzylsulfbnyl, 4-nitrobenzylsulfonyl, phenylethylsulfonyl, methanesulfonyl, ethylsulfonyl, propylsulfonyl, 2-methylpropylsulfonyl, 2-methylpropanylsulfonyl, cyclohexylmethylsulfonyl, cyclohexylethylsulfonyl, adamantylmethylsulfonyl or cyclopentylmethylsulfonyl.

In the present invention, coelenteramide or its analog which is used to produce the fluorescent protein includes the compounds described in the pamphlet of WO 2005/014633, page 42, line 19 to page 130, line 1, the compounds selected from the group consisting of the following compounds, and the like.

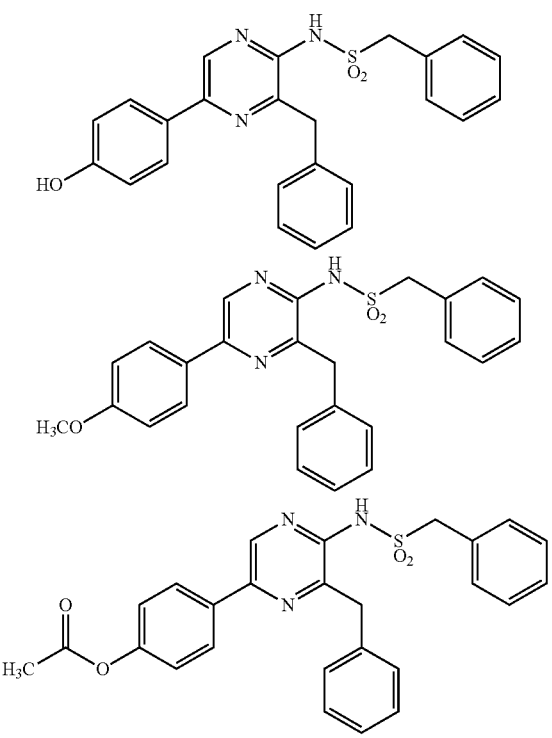

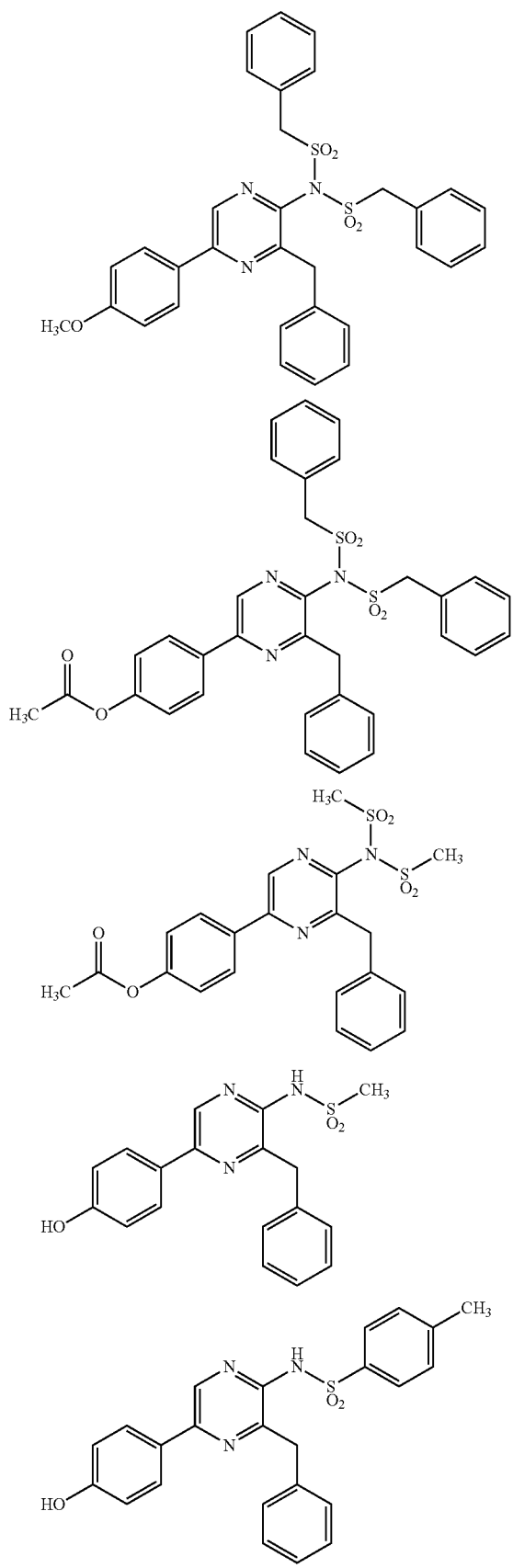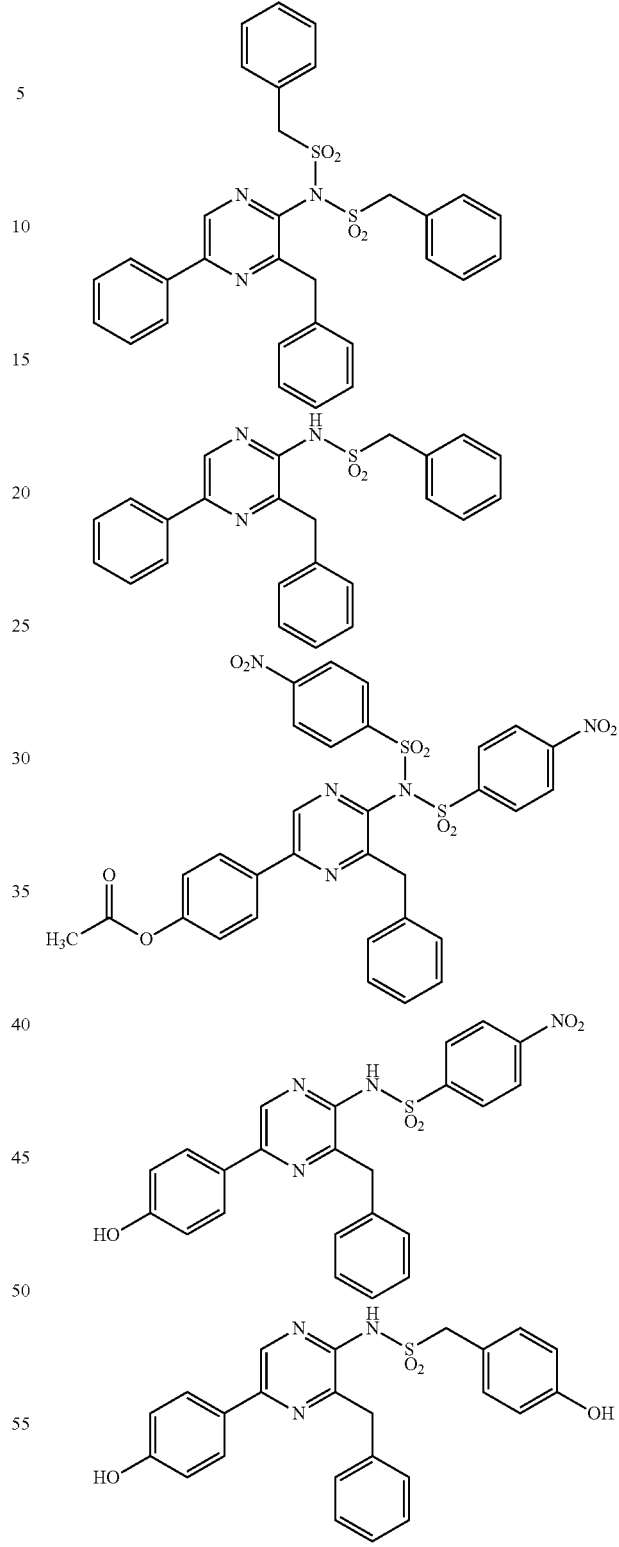
More preferred examples of the coelenteramide or its analog which is used to produce the fluorescent protein in the present invention include coelenteramide, e-coelenteramide and ch-coelenteramide
The coelenteramide or its analog can be produced by, for example, the method described in REFERENCE EXAMPLE 1 later given, the method described in Shimomura & Johnson, *Tetrahedron Lett.* (1973) 2963-2966, the method described in Teranishi & Goto, Bull, Chem, Soc. Jpn (1990) 63:3132-3140, the method described in Shimomura & Teranishi, Luminescence (2000) 15:51-58, or modifications of these methods.

Herein, in the compounds represented by general formula (1), the compound represented by general formula (2) below:

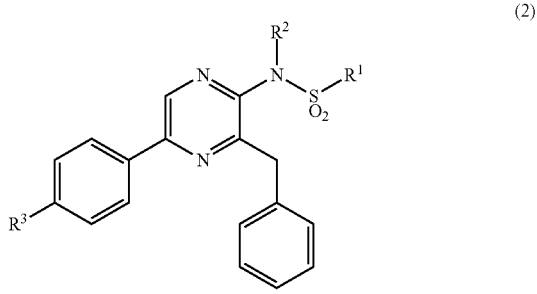

(2)

(wherein $R^1$, $R^2$ and $R^3$ are as defined above) can be produced by reacting the compound represented by general formula (4):

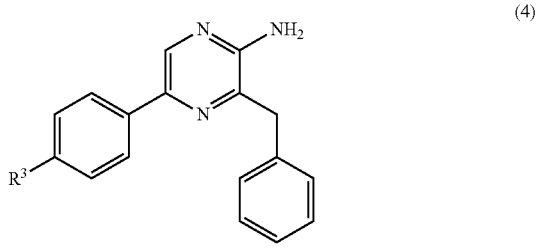

(4)

(wherein $R^3$ is as defined above) with the compound represented by general formula (5):

(5)

(wherein $R^1$ is as defined above).

The compound represented by general formula (4) can be produced by known processes. For example, the compound represented by general formula (4) can be produced by, for example, the methods described in Kishi, Y. et al., *Tetrahedron Lett.*, 13, 2747-2748 (1972) or Adamczyk, M. et al., *Org. Prep. Proced. Int.*, 33, 477-485 (2001), or modifications of these methods. More specifically, the compound represented by general formula (4) can be prepared as follows. First, cyclization of a substituted phenylglyoxal aldoxime and a glycinonitrile derivative is carried out using a Lewis acid catalyst such as titanium tetrachloride to form the pyrazine oxide. Subsequently, the pyrazine oxide is subjected to catalytic hydrogen reduction using Raney Ni, etc, as a catalyst to produce the compound. Alternatively, the compound can be produced through the Suzuki-Miyaura coupling reaction of a 2-amino-5-bromopyrazine derivative and a substituted phenyl pinacol boronate ester.

The compound represented by general formula (5) can be produced by known processes or is commercially available. Specifically, the compound can be produced by, for example, 1) reacting the corresponding substituted benzylsulfonic acid or its salt with an excess of thionyl chloride and heating the reaction mixture under reflux, followed by concentration under reduced pressure, or 2) reacting the corresponding substituted benzylsulfonic acid or its salt with the corresponding carboxylic acid chloride obtained by the treatment with oxalyl dichloride in a solvent such as dichloromethane in the presence of a catalytic amount of N,N-dimethylformamide (DMF) followed by concentration under reduced pressure, or 3) reacting a substituted benzyl Grignard reagent with sulfuryl chloride, or modifications thereof. Benzylsulfonic chloride can be purchased from Tokyo Chemical Industry Co., Ltd., Wako Pure Chemical Industries, Ltd., Kanto Chemical Co., Inc., etc.

Herein, the solvent used for the process of producing the compound represented by general formula (2) is not particularly limited and various solvents can be used, except for aqueous or alcoholic solvents. Examples of the solvent include pyridine, dichloromethane, chloroform, acetonitrile, tetrahydrofuran, ethyl acetate, acetone, toluene, dioxan, ether, and the like. These solvents can be used alone or as an admixture thereof.

In the process of producing the compound represented by general formula (2), the reaction temperature and reaction time are not particularly limited and include, for example, −20° C. to 200° C. for 0.25 to 72 hours, preferably −20° C. to 100° C. for 0.5 to 36 hours, and more preferably, 0° C. to 50° C. for an hour to 24 hours.

Furthermore, in the compounds represented by general formula (2), some compounds wherein $R^2$ is H, can be produced through alkali hydrolysis of the compound represented by $R^2$=$SO_2R^1$, i.e., the disulfonic amide compound to selectively cleave the sulfonic amide bond on one side only, or by modifications thereof.

In the compounds represented by general formula (1), the thioamide coelenteramide represented by general formula (3):

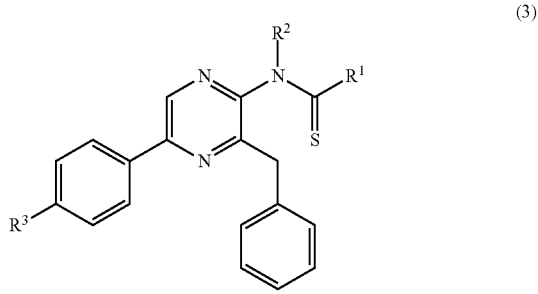

(3)

(wherein $R^1$, $R^2$ and $R^3$ are as defined above), can be produced by, e.g., reacting the compound represented by general formula (6):

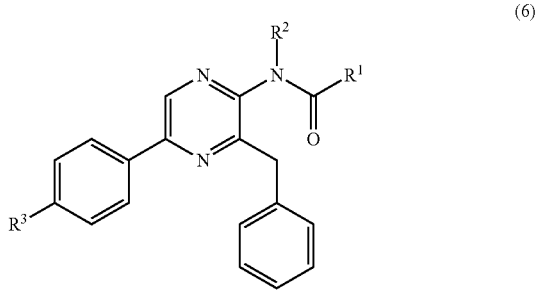

(6)

with Lawesson's reagent or phosphorus pentasulfide (tetraphosphorus decasulfide).

The compound represented by general formula (6) can be produced by known methods for production. Specifically, the compound can be produced by, e.g., reacting the compound represented by general formula (4) and the acid halide represented by general formula (7) or an analog thereof:

(7)

(wherein $R^1$ is as defined above and X is a halogen (e.g., fluorine, chlorine, bromine or iodine) or $R^1C(=O)-$) either in an organic solvent in the presence of a base, or in a basic organic solvent, or by modifications thereof.

Herein, the solvent used in the process of producing the compound represented by general formula (3) is not particularly limited unless it is an aqueous, alcohol, ketone and ester solvent. Examples of the solvent include toluene, benzene, dioxan, tetrahydrofuran, ether, dichloromethane, chloroform, pyridine and the like, which can be used alone or as an admixture thereof.

Further in the process of producing the compounds represented by general formula (3), the reaction temperature and reaction time are not particularly limited and include, for example, 0° C. to 200° C. for 0.5 to 72 hours, preferably room temperature to 200° C. for 1 to 48 hours, and more preferably, 60° C. to 150° C. for 2 to 24 hours.

The amount of coelenteramide or its analog used for producing the fluorescent protein is not particularly limited and is, for example, 1 mol to 5 mol, preferably 1 mol to 2 mol, and more preferably 1 mol to 1.2 mol, per mol of the protein of the invention.

In some embodiments of the present invention, divalent or trivalent ions that can be substituted for the calcium ions are used to produce the fluorescent protein. As used herein, the divalent or trivalent ions that can be substituted for the calcium ions refer to divalent or trivalent ions which cause a luminescence reaction when they are reacted with the calcium-binding photoprotein in place of calcium ions. In other words, the ions refer to ions that exert the similar function to calcium ions on a calcium-binding photoprotein. Examples of such ions include calcium ions ($Ca^{2+}$), magnesium ions ($Mg^{2+}$), strontium ions ($SR^{2+}$), barium ions ($Ba^{2+}$), lead ions ($Pb^{2+}$), cobalt ions ($Co^{2+}$), nickel ions ($Ni^{2+}$) cadmium ions ($Cd^{2+}$), yttrium ions ($Y^{3+}$), lanthanum ions ($La^{3+}$), samarium ions ($Sm^{3+}$), europium ions ($Eu^{3+}$), dysprosium ions ($Dy^{3+}$), thulium ions ($Tm^{3+}$), and yttribium ions ($Yb^{3+}$). Of these ions, divalent metal ions are preferred and divalent ions of metals other than transition metals (e.g., $Ca^{2+}$, $SR^{2+}$ and $Pb^{2+}$) are more preferred.

Where calcium ions or the divalent or trivalent ions that can be substituted for the calcium ions are used, the amount is not particularly limited and is, for example, 4 mol to 10 mol, 10 mol to 100 mol, 100 mol to 1000 mol, etc., per mol of the protein of the invention.

In the production of the fluorescent protein of the invention, the reaction of the protein of the invention with coelenteramide and its analog is preferably carried out in the presence of a reducing agent. Examples of the reducing agent used herein include dithiothreitol (DTT), mercaptoethanol and the like. The amount of the reducing agent used to produce the fluorescent protein of the invention is not particularly limited unless it affects the reconstitution of the fluorescent protein of the invention. When two or more cysteine residues are present in the protein of the invention, the reducing agent is preferably set at a concentration so as to prevent S—S bond formation. For example, 1 mM dithiothreitol or 0.1% mercaptoethanol is preferred.

In some embodiments of the present invention, the reaction between the protein of the invention and coelenteramide or its analog is carried out in the presence of a chelating agent to remove calcium ions or the divalent or trivalent ions that can be substituted for the calcium ions. In this case, the amount of the chelating agent is not particularly limited unless it affects production of the fluorescent protein. It is shown that 3 mol of calcium ions are bound to 1 mol of the protein of the invention in its ionic state. Therefore, it is preferred to use at least 3 mol of the chelating agent.

The chelating agent used to produce the fluorescent protein may be any one and is not particularly limited, so long as it strongly binds to calcium ions or the divalent or trivalent ions that can be substituted for the calcium ions. Examples of the chelating agent include ethylenediaminetetraacetic acid (EDTA), ethyleneglycol bis(β-aminoethyl ether)-N,N,N',N'-tetraacetic acid (EGTA), trans-1,2-diaminocyclohexane-N,N,N',N'-tetraacetic acid (CyDTA), N-(2-hydroxyethyl)iminodiacetic acid (HIDA), and the like.

In the production of the fluorescent protein, the reaction temperature and reaction time are not particularly limited and include, for example, 0° C. to 42° C. for 0.1 to 2 hours, 4° C. to 37° C. for 0.1 to 2 hours, or 4° C. to 15° C. for 0.1 to 24 hours.

The fluorescent protein thus obtained may be further purified. The purification of gFP can be performed by conventional methods for separation/purification. Examples of methods for separation/purification include ammonium sulfate precipitation, gel filtration chromatography, ion-exchange chromatography, affinity chromatography, reversed phase high performance liquid chromatography, dialysis, ultrafiltration, etc., which may be used solely or in a suitable combination.

7.2. Use of Fluorescent Protein (1) Use as Reporter Protein

The fluorescent protein of the invention can be used also as a reporter protein to assay the transcription activity of a promoter or the like. For example, the polynucleotide encoding the protein of the invention is fused to a target promoter or some other expression control sequence (e.g., an enhancer, etc.) to construct a vector. The resulting vector is introduced into a host cell, with which coelenteramide or its analog is brought in contact in the presence or absence of calcium ions or the divalent or trivalent ion that can be substituted for the calcium ions to produce the fluorescent protein. By detecting the fluorescence generated from the fluorescent protein of the invention, the activity of the target promoter or some other expression control sequence can be assayed (2) Use as Marker for Detection The fluorescent protein of the invention can be used as a marker for detection by fluorescence. The detection marker is available for the detection of a target substance in, for example, an immunoassay or hybridization assay. The fluorescent protein can be used by binding to a target substance (a protein or a nuclei acid) in a conventional manner such as chemical modifications. Such detection markers can be used for the detection in a conventional manner. The detection marker of the invention can also be used to determine the distribution of a target protein by expressing the marker as a fusion protein to the target substance, inserting the fusion protein into a cell by means of microinjection, etc. and further bringing coelenteramide or its analog in contact therewith in the presence or absence of calcium ions or the divalent or trivalent ion that can be substituted for the calcium ions thereby to form the fluorescent protein. The distribution of a target substance can be determined by a method for detection such as fluorescence imaging. The apoprotein can also be used after expression in a cell, in addition to the insertion into a cell by means of microinjection, etc.

(3) Material for Amusement Product

The fluorescent protein of the invention can be suitably used as a fluorescent substrate in materials for amusement products. Examples of amusement products include fluorescent bubble soap, fluorescent ice, fluorescent candies and fluorescent paints. The amusement products can be prepared in a conventional manner Where no particular explanation is given for the embodiments or examples to carry out the invention, there may be used the methods described in standard protocols such as J. Sambrook, E. F Fritsch & T. Maniatis (Ed.), Molecular Cloning, A Laboratory Manual (3$^{rd}$ edition), Cold Spring Harbor Press, Cold Spring Harbor, New York (2001); F. M. Ausubel, R. Brent, R. E. Kingston, D. D. Moore, J. O, Seidman, J. A. Smith, K, Struhl (Ed.), Current Protocols in Molecular Biology, John Wiley & Sons Ltd.; or modifications or variations thereof. When commercially available reagent kits and measurement equipments are used, the protocols attached thereto are used, unless otherwise indicated.

All literatures and publications mentioned in this specification are herein incorporated in their entirety by reference into the specification, irrespective of their purposes. This specification includes all of the contents as disclosed in the claims, specification and/or drawings of Japanese Patent Application No. 2009-117972 filed on May 14, 2009, which is a priority document of the present application.

The objects, features, advantages and ideas of the invention will be apparent to those skilled in the art from the description herein, and those skilled in the art will be able to readily perform the invention. The best mode for carrying out the invention and specific examples, etc. which show preferred embodiments of the invention, are given by way of illustration or explanation, and are not intended to limit the invention thereto. It will be apparent to those skilled in the art that various modifications may be made based on described aspects in the specification without departing from the spirit and scope of the invention disclosed herein.

Sequence numbers in the Sequence Listing herein indicate the following sequences.

SEQ ID NO: 1 shows the nucleotide sequence of DNA of CLI-ESNA. This nucleotide sequence shows the nucleotide sequence at positions 88 to 657 in SEQ ID NO: 3 or the nucleotide sequence at positions 112 to 681 in SEQ NO; 5.

SEQ ID NO: 2 shows the amino acid sequence of CLI-ESNA. This amino acid sequence shows the amino acid sequence at positions 30 to 218 in SEQ ID NO; 4 or the amino acid sequence at positions 38 to 226 in SEQ ID NO: 6.

SEQ ID NO: 3 shows the nucleotide sequence of DNA encoding the protein bearing CLI-ESNA, which was inserted into the expression vector Blu-CLI-ESNA constructed in EXAMPLE 1.

SEQ ID NO: 4 shows the amino acid sequence of the protein bearing CLI-ESNA encoded by the expression vector pBlu-CLI-ESNA constructed in EXAMPLE 1.

SEQ ID NO: 5 shows the nucleotide sequence of DNA encoding the protein bearing CLI-ESNA, which was inserted into the expression vector piP-H-CLI-ESNA constructed in EXAMPLE 3.

SEQ ID NO: 6 shows the amino acid sequence of the protein bearing CLI-ESNA, which is expressed by the expression vector piP-H-CLI-ESNA constructed in EXAMPLE 3.

SEQ ID NO: 7 shows the nucleotide sequence of primer CLI-1N/Xbal used in EXAMPLE 1.

SEQ ID NO: 8 shows the nucleotide sequence of primer CL-I_S140P-R used in EXAMPLE 1.

SEQ ID NO: 9 shows the nucleotide sequence of primer CL-I_S140P-F used in EXAMPLE 1.

SEQ ID NO: 10 shows the nucleotide sequence of primer CLI-2-C/SalI used in EXAMPLE 1.

SEQ ID NO; 11 shows the nucleotide sequence of primer CL-I_E110D-R used in EXAMPLE 1.

SEQ ID NO: 12 shows the nucleotide sequence of primer CL-I_E110D-F used in EXAMPLE 1.

SEQ ID NO: 13 shows the nucleotide sequence of primer CL*28_N179T,A180S-R used in EXAMPLE 1.

SEQ ID NO: 14 shows the nucleotide sequence of primer CLI-N-EL-SacI used in EXAMPLE 3.

SEQ ID NO: 15 shows the nucleotide sequence of primer CLI-C-XboI used in EXAMPLE 3.

SEQ ID NO; 16 shows the nucleotide sequence of cDNA clone ph41 of CLI.

SEQ ID NO: 17 shows the amino acid sequence deduced from the nucleotide sequence of cDNA clone ph41 of CLI.

SEQ ID NO: 18 shows the nucleotide sequence of CLI. This nucleotide sequence shows the nucleotide sequence at positions 28 to 597 in SEQ ID NO: 16.

SEQ ID NO: 19 shows the amino acid sequence of CU. This amino acid sequence shows the amino acid sequence at positions 10 to 198 in SEQ ID NO: 17.

Hereinafter., the present invention is described by referring to EXAMPLES but is not deemed to be limited thereto.

EXAMPLE 1

Construction of Recombinant Apoclytin Gene

The apoclytin gene fragmemt was obtained by PCR using apoclytin gene encoding apoclytin as a template, and was inserted into a expression vector pBlueScript SK(+) (Stratagem) and the luminescence patterns were analyzed.

Specifically, pBlue-CLI-ESNA was constructed by the following procedures.

PCR was carried out using a PCR kit (manufactured by Takara Bio) with pPh41(described in FEBS Lett. 315 (1993) 343-346) as a template and two PCR primers of CLI-1N/XbaI (5' c ggTCTAGAA GTC AAA CTC AGA CCC AAC TTC 3' (SEQ ID NO: 7)) and CL-I_S140P-R(5' GTC TGA TGG GCA GAT TCC AGA 3' (SEQ ID NO: 8)) (cycle conditions: with 25 cycles of 1 min./94° C., 1 min/50° C. and 1 min./72° C.). In a similar manner, PCR was performed using the PCR kit with pPH41 as a template and two PCR primers of CL-I_S140P-F (5' ATC TGC CCA TCA GAC GAA GAC 3' (SEQ ID NO: 9)) and CLI-2-C/SalI (5' ggc GTC GAC TTA AGO AAC AAA ATT GCC OTA 3 (SEQ ID NO: 10)). PCR was performed using the PCR kit with the resulting each DNA fragment as a template and two PCR primers of CLI-1N/XbaI and CLI-2-C/SalI to amplify the desired apoclytin gene region. The resulting DNA fragment was purified using a PCR purification kit (manufactured by Qiagen). The purified DNA fragment was then digested with restriction enzymes XbaI/SalI in a conventional manner, and ligated into the restriction enzyme XbaI/SalI sites on pBlue-ScriptSK(+) (Stratagene), thereby to construct the expression vector pBlue-CL-S140P. The nucleotide sequence was determined using a DNA sequencer (manufactured by ABI) to confirm the insert DNA.

Next, PCR was performed using a PCR kit with pBlue-CL-S140P as a template and two PCR primers of CLI-1N/XbaI and CL-I_E110D-R (5' AAC AGC ATC TCC CCA GTC GCG 3' (SEQ ID NO: 11)). PCR was performed using the PCR kit similarly with pBlue-CL-S140P as the template and two PCR primers of CL-I_E110D-F (5' TOG GGA GAT GCT GTT TTC GAC 3' (SEQ ID NO: 12)) and CL*28_N179T,A180S-R (5' ggc GTC GAC TTA AGG AAC AAA ATT GCC GTA AAG ACC ATC ACT AGT GGG 3' (SEQ ID NO: 13)). PCR was performed using a PCR kit with the resulting each DNA fragment as a template and the two PCR primers of CU-1N/XbaI and CL*28_N179T, A180S-R to amplify the desired apoclytin gene region. The resulting DNA fragment was purified using the PCR purification kit. The purified DNA fragment was then digested with restriction enzymes XbaI/SalI in a conventional manner and ligated into the restriction enzyme XbaI/SalI sites on pBlueScriptSK(+) (Stratagene), thereby to construct the expression vector pBlue-CLI-ESNA (FIG. 1).

The nucleotide sequence was determined using a DNA sequencer (manufactured by ABI) to confirm the insert DNA. The nucleotide sequence of DNA encoding recombinant apoclytin-ESNA inserted into p.Blue-CLI-ESNA is shown by SEQ ID NO: 3. The amino acid sequence of the protein encoded by the polynucleotide consisting of the nucleotide sequence represented by SEQ ID NO: 3 is shown by SEQ ID NO: 4.

EXAMPLE 2

Expression of Recombinant Apoclytin in *E. coli*

The recombinant apoclytin gene was expressed in *E. coli*, using host *E. coli* JM83 (ATCC Accession No. 35607) bearing the vector prepared in EXAMPLE 1 wherein the recombinant apoclytin gene was inserted into pBiueScript SK(+). The transformant was inoculated onto 10 ml of LB liquid medium (10 g of bactotryptone, 5 g of yeast extract and 5 g of sodium chloride per liter of water; pH 7.2) containing ampicillin (100 µg/ml) followed by further incubation at 37° C. for 18 hours. The cultured cells were harvested by centrifugation for 5 minutes at 10,000 rpm using a cooling centrifuge, and suspended in 30 mM Tris-HCl (pH 7.6) containing 10 mM EDTA. The suspension was ultrasonicated (manufactured by Branson, Sonifier model 250) on ice to recover the supernatant.

EXAMPLE 3

Construction of Recombinant Apoclytin-ESNA Expression Vector (piP-H-CLI-ESNA)

In order to express recombinant apoclytin-ESNA in *E. coli*, expression vector piP-H-CLI-ESNA was obtained by inserting pBlue-CLI-ESNA bearing the recombinant apoclytin-ESNA gene, which was prepared by PCR, into the expression vector piP-H-M(11) described in EXAMPLE 4 of JPA 2008-22848.

Specifically, the recombinant apoclytin-ESNA expression vector piP-H-CLI-ESNA was constructed by the following procedures.

PCR was performed using a PCR kit with recombinant apoclytin-ESNA gene-bearing pBlue-CLI-ESNA as a template and two PCR primers of CLI-N-EL-SacI (5' ggc gAgCTC AGA CCC AAC TTC GAC AAC 3' (SEQ ID NO: 14), wherein the SacI restriction enzyme site is underlined) and CLI-C-XhoI (5' cgg CTCGAG TTA AGG AAC AAA ATT GCC GTA 3' (SEQ ID NO: 15), wherein the XhoI restriction enzyme site is underlined) to amplify the desired recombinant apoclytin-ESNA gene region. The resulting DNA fragment was purified using the PCR purification kit. The purified DNA fragment was then digested with restriction enzymes SacI/XhoI in a conventional manner, and ligated into the restriction enzyme SacI/XhoI sites on piP-H-M(11), thereby to construct vector piP-H-CLI-ESNA shown in FIG. 2.

The nucleotide sequence was determined using a DNA sequencer (manufactured by ABI) to confirm the insert DNA. The nucleotide sequence of DNA encoding recombinant apoclytin-ESNA inserted into piP-H-CLI-ESNA is shown by SEQ ID NO: 5. The amino acid sequence of the protein encoded by the polynucleotide consisting of the nucleotide sequence represented by SEQ ID NO: 5 is shown by SEQ ID NO: 6.

EXAMPLE 4

Purification of Protein
1) Expression of Protein in *E. coli*

The expression vector piP-H-CLI-ESNA was transformed into *E. coli* strain WA802 (ATCC Accession No. 33526) in a conventional manner. The resulting transformant was inoculated onto 10 ml of LB liquid medium (10 g of bactotryptone, 5 g of yeast extract and 5 g of sodium chloride per liter of water; pH 7.2) containing ampicillin (100 µg/ml) followed by further incubation at 37° C. for 18 hours. The cultured cells were added to 2 liters of fresh LB liquid medium (400 ml×5) and cultured at 37° C. for 18 hours. The cultured cells were then harvested by centrifugation for 5 minutes at 5,000 rpm (6,000×g) using a cooling centrifuge.

2) Extraction of apoclytin-ESNA Protein from Cultured Cells

The cells harvested in 1) above were suspended in 200 ml (40 ml×5) of 50 mM Tris-HCl (pH 7.6), and sonicated three times for 3 minutes each on ice (manufactured by Branson, Sonifier model 250). The cell lysate was then centrifuged at 10,000 rpm (12,000×g) for 20 minutes. The resulting soluble fraction was used as the starting material for purification of apoclytin-ESNA protein.

3) Purification of Recombinant apoclytin-ESNA Protein by Nickel Chelate Column Chromatography The soluble fraction (200 ml) obtained in 2) above was applied to a nickel chelate column (Amersham Bioscience; column size: 6.5 cm in diameter×2.5 cm), which had been equilibrated with 50 mM Tris-HCl (pH 7.6) to adsorb the recombinant apoclytin-ESNA protein. After washing with 200 ml of 50 mM Tris-HCl (pH 7.6), the adsorbed recombinant apoclytin-ESNA protein was eluted with 0.1M imidazole (Wako Pure Chemical Industries). The luminescence activity of each fraction was assayed and the fractions having the luminescence activity were collected.

4) Regeneration of Recombinant apoclytin-ESNA Protein into Recombinant clytin-ESNA Protein The recombinant apoclytin-ESNA protein was regenerated to the recombinant clytin-ESNA protein under the following conditions.

The purified recombinant apoclytin-ESNA protein (20 ml) obtained in 3) above was dissolved in 80 ml of 50 mM Tris-HCl (pH 7.6) containing 10 mM DTT and 10 mM EDTA, and 0.4 mg of coelenterazine dissolved in ethanol was added to the solution. The mixture was allowed to stand at 4° C. overnight thereby to regenrate to the recombinant clytin-ESNA protein, 5) Purification of Recombinant clytin-ESNA Protein by Butyl Sepharose Column Chromatography To separate the recombinant clytin-ESNA protein which formed a complex with coelenterazine from the recombinant apoclytin-ESNA protein which did not form the complex, the hydrophobic chromatography using Butyl Sepharose 4 Fast Flow Gel was perfomed. That is, the recombinant clytin-ESNA protein (150 ml) obtained in 4) above was adjusted to 2M in a final concentration of ammonium sulfate. Next, the insoluble fraction was removed by centrifugation. The supernatant was adsorbed to a Butyl Sepharose 4 Fast Flow column (Amersham Bioscience, column size, 6.0 cm in diameter×1.5 cm), which had been equilibrated with 10 mM Tris-HCl, 2 mM EDTA (pH 7.6) containing 2M ammonium sulfate, and then the column was washed with 2M ammonium sulfate. After elution with 1.2M ammonium sulfate, the recombinant clytin-ESNA fraction having the luminescence activity was recovered. On the other hand, the recombinant apoclytin-ESNA was only eluted with 10 mM Tris-HCl, 2 mM EDTA (pH 7.6).

The protein concentration was determined by a commercial kit (manufactured by BioRad) by the method of Bradford, using bovine serum albumin (manufactured by Pierce) as a standard.

Figure 3:
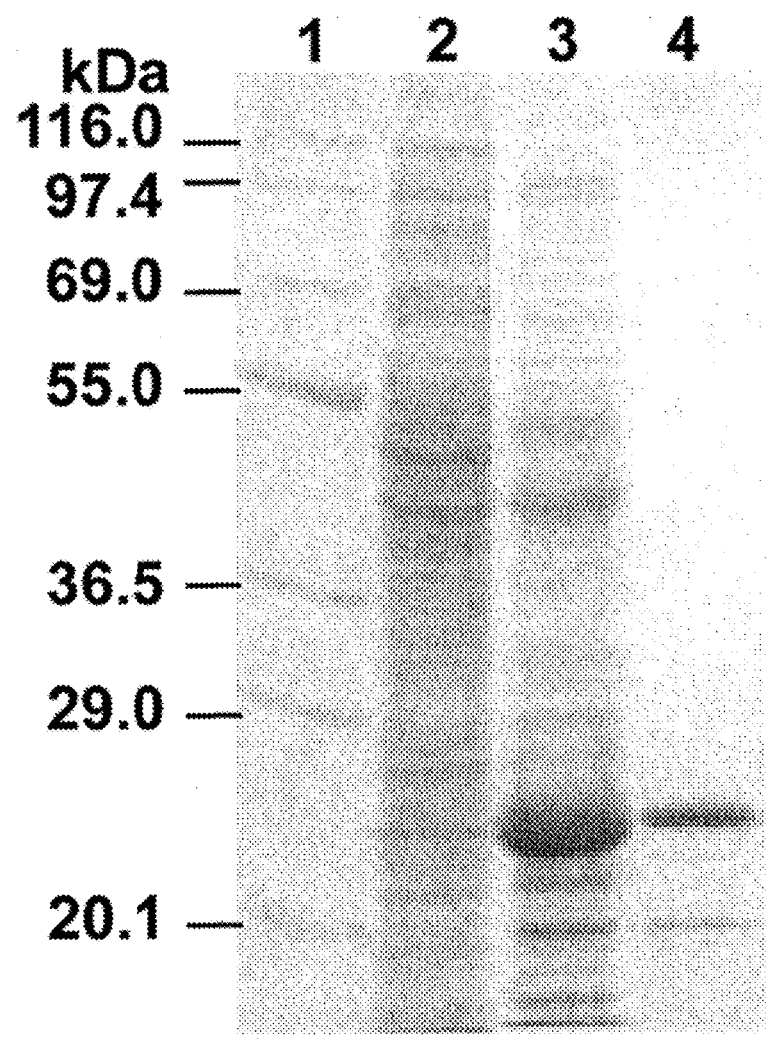
FIG. 3 shows the results of SDS-PAGE analysis (EXAMPLE 4). Lane 1: Protein molecular weight markers (Tefco), Lane 2: Supernatant (corresponding to 100 µl of the cultured bacterial cells) obtained by centrifugation at 5,000 g for 10 minutes from the ultrasonicated lysate of transformants expressing piP-H-CLI-ESNA in *E. coli*; Lane 3: Fraction eluted from a nickel-chelate column (protein level, 29.5 µg); Lane 4: Fraction eluted from a butyl sepharose column (protein level, 2.2 µg).

SDS-PAGE analysis was performed on each fraction obtained from each purification step under reducing conditions using a 12% polyacrylamide gel. FIG. 3 shows the results of SDS-PAGE analysis. From 2 liters of the cultured cells, 5.3 mg of the recombinant clytin-ESNA was obtained in a purity of 95%.

EXAMPLE 5

Measurement of Luminescence Activity

The luminescence activity of the recombinant clytin-ESNA of EXAMPLE 4 was measured as follows. After mixing 2-mercaptoethanol (1 μl) and substrate coelenterazine (1 μg/μl dissolved in ethanol) with 30 mM Tris-HCl (pH 7.6) containing 10 mM EDTA, the recombinant apoclytin-ESNA at each purification step was added to the mixture. The reaction was carried out on ice (4° C.) for 2 hours to regenerate recombinant clytin-ESNA. The luminescence reaction was triggered by adding a 50 mM calcium solution (100 μl/well) to 1 μl of this regenerated recombinant clytin-ESNA solution. The luminescence activity was measured for 10 seconds using a luminescence plate reader Centro LB960 (manufactured by Berthold) and expressed in terms of the maximum luminescence intensity (Imax).

EXAMPLE 6

Comparison of Recombinant clytin-ESNA with Other Photoproteins for Luminescence Activity In order to compare the luminescence properties between the recombinant clytin-ESNA (CLI-ESNA) obtained in EXAMPLE 5 and other holoproteins (aequorin (AQ)), clylin-I (CL-I), clytin-II (CL-II)) and obelin (Ob)), the luminescence patterns triggered by the addition of calcium were compared.

The luminescence patterns of CLI-ESNA, AQ, CL-I, CL-II and Ob were measured as follows. 2-Mercaptoethanol (1 μl) and a solution of substrate coelenterazine (1 μg/μl) in ethanol were mixed with 30 mM Tris-HCl (pH 7.6) containing 10 mM EDTA. Each of CLI-ESNA, AQ, CL-I, CL-II and Ob was then added to the mixture and the reaction was carried out for 2 hours on ice (4° C.) for reconstitution, respectively. The luminescence reaction was initiated by adding 100 μl/well of a 50 mM calcium solution to this reconstitution solution. The luminescence activity was measured for 10 seconds using a luminescence plate reader Centro LB960 (manufactured by Berthold) and expressed in terms of the maximum luminescence intensity (Imax).

Figure 4:
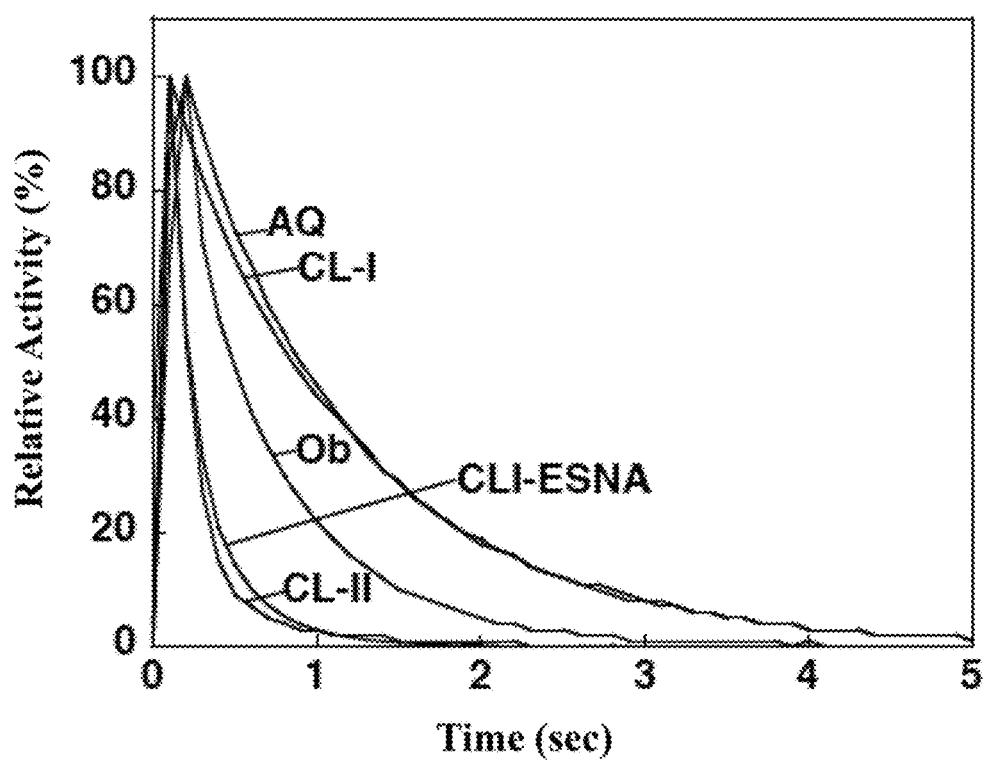
FIG. 4 shows the measurement results of luminescence patterns for CLA-ESNA, AQ (aequorin), CL-I (clytin-II) and Ob (obelin) (EXAMPLE 6).

The results are shown in FIG. 4. As shown in FIG. 4, the luminescence patterns were compared between the recombinant clytin and other photoproteins for their relative luminescence activities. The recombinant clytin-ESNA showed a rapid decay pattern of the luminescence patterns as compared to AQ, CI-I, Ob, etc. The results reveal that the recombinant clytin-ESNA reconstituted from the recombinant apoclytin-ESNA having 4 amino acid mutations shows a higher S/N ratio than Cl-I.

REFERENCE EXAMPLE 1

Synthesis of Coelenteramide

4-Methoxyphenylacetyl chloride (Aldrich), 1.0M $CH_2Cl_2$ solution of $BBr_3$ (Aldrich) and all other chemical reagents used in the synthesis are commercially available and used as provided.

In thin layer chromatography (TLC) for analysis, a silica gel plate precoated with silica gel (0.25 mm) (MERCK, Silica gel 60 $F_{254}$, Catalogue No. 1.05715.0009) was used.

For preparatory column chromatography, silica gel (Kanto Chemical, silica gel 60N, spherical, neutral, Catalogue No. 37563-84) was used.

Melting points (Mp.) were measured on YANACO MP-J3 (uncorrected), $^1H$ (300 MHz) nuclear magnetic resonance spectra (NMR spectra) and $^{13}C$ (75.5 MHz)

NMR spectra were measured in DMSO-$d_6$ (CIL) on a Varian Gemini-300. The $^1H$ NMR chemical shifts were referenced to the peak of a residual non-deuterated dimethylsulfoxide in a measurement solvent DMSO-$d_6$ set at δ 2.49 as a standard. The $^{13}C$ NMR chemical shifts were referenced to the peak of measurement solvent DMSO-$d_6$ set at δ 39.7 as a standard. The chemical shifts are indicated by unit ppm, respectively. The binding constant (J) is given by unit Hz. Abbreviations s, m and hr designate singlet, multiplet and broad, respectively. Infrared spectroscopic (IR) spectrum was measured by diffuse reflectance spectroscopy using a spectrometer SHIMADZU IRPrestige-21 equipped with DRS-8000A. The absorption zone was shown by unit $cm^{-1}$. High resolution mass spectrometry (HRMS) was performed using a mass spectrometer EOL JMS-700 under the conditions for electron impact ionization (EI).

Synthetic Scheme of Coelenteramide

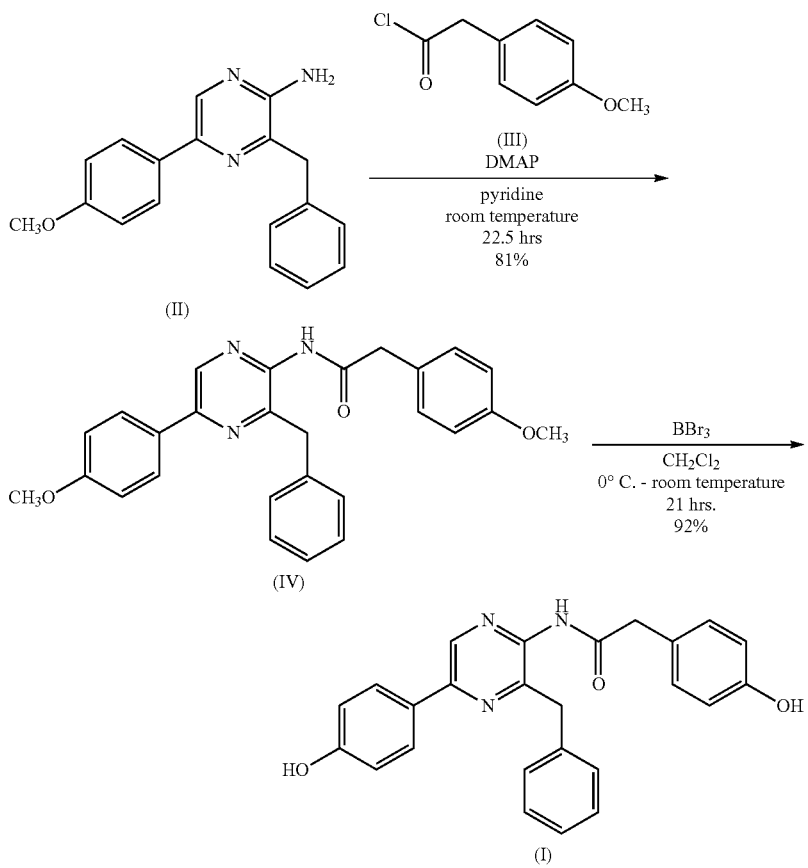

Coelenteramide Dimethyl Ether (IV)

In an argon atmosphere, 4-(dimethylamino)pyridine (DMAP) (21.1 mg, 172 μmol) and 4-methoxyphenylacetyl chloride (III) (527 μL, 3.45 mmol) were subsequently added to a solution (5 mL) of 2-amino-3-benzyl-5-(4-methoxyphenyl)pyrazine (II) (also known as coelenteramine methyl ether) (Kishi et al., Tetrahedron Lett., 13, 2747-2748 (1972); Adamczyk et al. Org. Prep. Proced. Int., 33, 477-485 (2001)) (502 mg, 1.72 mmol) in pyridine at room temperature. The resulting mixture was agitated at the same temperature for 2.5 hours. Saturated sodium hydrogencarbonate aqueous solution (100 mL) was added to the mixture. Extraction of the mixture was performed using dichloromethane (50 mL×3). The organic extract was dried over anhydrous sodium sulfate, filtered and concentrated under reduced pressure. The residual pyridine was removed azeotropically with toluene (20 mL×3). The residue was purified by silica gel chromatography (85 g, dichloromethane/ethyl acetate=9/1) to give coelenteramide dimethyl ether (IV) (617 mg, 81.5%) as a pale yellow solid. Recrystallization from ethyl acetate cave a colorless solid as an analytically pure sample (recrystallization twice in total gave 458 mg, 60.5%), Mp. 189.5-191° C.; $^1$H NMR (300 MHz, DMSO-$d_6$) δ3.61 (s, 2H)3.73 (s, 3H), 3.80 (s, 3H), 4.03 (s, 2H), 6.88-6.93 (AA'BB', 2H), 7.02-7.07 (2×AA'BB', 4H), 7.12-7.30 (m, 5H), 8.00-8.05 (AA'BB', 2H), 8.87 (s, $^1$H), 10.43 (s, $^1$H); $^{13}$C NMR (75.5 MHz, DMSO-$d_6$) δ 41.6, 55.1, 55.3, 113.9 (2C), 114.5 (2C), 126.2, 127.5, 128.0(2C), 128.1, 128.2 (2C), 129.0 (2C), 130.2 (2C), 137.1, 138.3, 143.7, 148.2, 150.5, 158.2, 160.7, 170.3; IR (KBr, cm$^{-1}$) 698, 833, 1034, 1177, 1256, 1495, 1514, 1543, 1672, 2833, 2957, 3265; HRMS (EI) m/z 439.1898 (M$^+$, $C_{27}H_{25}N_3O_3$ requires 439.1896).

Coelenteramide (I)

In an argon atmosphere, a solution (20 mL) of coelenteramide dimethyl ether (IV)(660 mg, 1.50 mmol) was added to 1.0 M dichloromethane solution of boron tribromide (6.01 mL, 6.01 mmol) at 0° C. over 10 minutes. The mixture was agitated at the same temperature for 15 minutes. The mixture was warmed to room temperature. The agitation was continued for 21 hours. Saturated sodium hydrogencarbonate (100 mL) was added to the mixture. The mixture was concentrated under reduced pressure to remove dichloromethane. The residual aqueous suspension was filtered. The solid recovered was dried in vacuum to give coelenteramide (I) (570 mg, 92.3%) as a pale yellow solid.

Recrystallization from ethanol gave a colorless solid (103 mg, 16.7%) as an analytically pure sample.

Mp. 242-243° C. (dec.); $^1$H NMR (300 MHz, DMSO-$d_6$) δ 3.54 (s, 2H), 4.01 (s, 2H), 6.69-6.75 (AA'BB', 2H), 6.84-6.90 (AA'BB', 2H), 7.00-7.06 (AA'BB', 2H), 7.11-7.24 (m, 5H), 7.89-7.95 (AA'BB', 2H), 8.80 (s, $^1$H), 9.28 (br s, $^1$H), 9.85 (br s, $^1$H), 10.35 (s, $^1$H); $^{13}$C NMR (75.5 MHz, DMSO-$d_6$) δ 41.7, 115.2 (2C), 115.8 (2C), 125.7, 126.2, 126.6, 128.0 (2C), 128.2 (2C), 129.0 (2C), 130.2 (2C), 136.8, 138.4, 143.4, 148.6, 150.5, 156.2, 159.1, 170.5; IR (KBr, cm$^{-1}$) 704, 1157, 1229, 1267, 1364, 1450, 1493, 1516, 1545, 1593, 1611, 1673, 3022, 3285, 3385; HRMS (EI) m/z 411.1582 (M+, $C_{25}H_{21}N_3O_3$ requires 411.1583).

EXAMPLE 7

Figure 5:
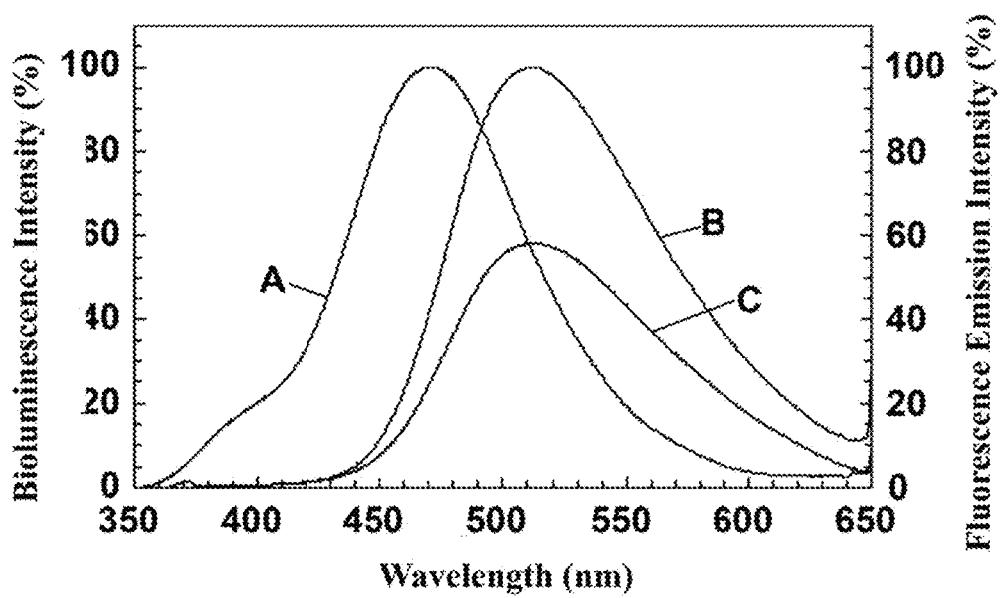
FIG. 5 shows the bioluminescence spectrum of recombinant clytin-ESNA and the fluorescence spectrum of the synthetic fluorescent proteins prepared from recombinant apoclytin-ESNA and coelenteramide.

Preparation of Novel Synthetic Fluorescent Proteins from Coelenteramide and Recombinant Apoclytin-ESNA Recombinant apoclytin-ESNA (0.5 mg, 22 nmol) (the product obtained in EXAMPLE 4, 3)) was mixed with 10 µl of coelenteramide (1.2 µg/µl in anhydrous methanol, 29 nmol)(the product obtained in REFERENCE EXAMPLE 1) in 1 ml of 50 mM Tris-HCl (pH 7.6) containing 10 mM $CaCl_2$ and 1 mM DTT. The mixture was allowed to stand at 4° C. for 16 hours to synthesize a fluorescent protein. Subsequently, the photoprotein was treated at 4° C. under 5,000×g for 20 minutes using a centrifugal concentrator Amicon Ultra-4 (10,000 MWCO, MILLIPORE) to remove an excess of coelenteramide, thereby to concentrate the mixture to 0 ml. The concentrated solution showed a strong yellow fluorescence under a long-wavelength UV lamp (366 nm). As shown in FIG. 5, the fluorescence spectrum having the fluorescence maximum wavelength at 513 nm was obtained by excitation at wavelength 335 nm (spectrum B in FIG. 5).

EXAMPLE 8

Preparation of Calcium-Free Novel Synthgtic Fluorescent Proteins from Coelenteramide and Recombinant Apoclytin-ESNA Recombinant apoclytin-ESNA (0.5 mg, 22 nmol) (the product obtained in EXAMPLE 4, 3)) was mixed with 10 µl of coeleriteramide (1.2 µg/µl in anhydrous methanol, 29 nmol)(the product obtained in REFERENCE EXAMPLE 1) in 1 ml of 50 mM Tris-HCl (pH 7.6) containing 10 mM EDTA and 1 mM DTT. The mixture was allowed to stand at 4° C. for 16 hours to synthesize a calcium-free fluorescent protein. Subsequently, the photoprotein was treated at 4° C. under 5,000×g for 20 minutes using a centrifugal concentrator Amicon Ultra-4 (10,000 MWCO, MILLIPORE) to remove an excess of coelenteramide, thereby to concentrate the mixture to 0.1 ml. As shown in FIG. 5, the fluorescence spectrum having the fluorescence maximum wavelength at 513 nm was obtained by excitation at wavelength 335 nm (spectrum C in FIG. 5).

EXAMPLE 9

Measurement of Fluorescence and Bioluminescence Emission Spectra

Fluorescence spectra of the synthetic fluorescent proteins in EXAMPLES 7 and 8 were measured at 25° C. in a quartz cell (optical path length: 10 mm) using a Jasco FP-6500 spectrofluorimeter (band width for emission/excitation: 3 nm, responses 0.5 sec, scan speed: 100 nm/min).

Bioluminescence emission spectra of the recombinant clytin-ESNA obtained in EXAMPLE 4, 5) were measured in a quartz cell having a 10 mm optical path under the given conditions (band width for emission/excitation: 20 nm, response: 0.5 sec, scan speed: 2000 nm/min) using a fluorescence spectrophotometer (JASCO FP-6500) with the excitation source turned off. As shown in FIG. 5, the emission spectrum having the emission maximum wavelength at 470 nm was obtained by adding 0.1 ml of 50 mM $CaCl_2$ to 1 ml of 50 mM Tris-HCl (pH 7.6) containing the purified recombinant clytin-ESNA (0.02 mg) (spectrum A in FIG. 5).

Correction was made for the fluorescence and bioluminescence emission spectra thus obtained.

As shown in FIG. 5, the fluorescence spectra obtained from the synthetic fluorescent proteins in EXAMPLES 7 and 8 showed the emission maximum wavelength of 513 nm, which shifted toward a longer wavelength by about 43 nm or more. That is, the novel fluorescent proteins showing markedly different fluorescence spectra from bioluminescence emission spectra could be prepared from apoclytin-ESNA.

The protein of the present invention can form the holoprotein composed of the protein of the present invention and the peroxide of coelenterazine as a luminescence substrate. The holoprotein of the invention exists as a complex produced from the protein of the invention and the peroxide of coelenterazine. When calcium ions are bound to the complex, a flash of light is emitted. This luminescence shows at least one of the excellent properties that the decay of luminescence is rapid and the S/N ratio is excellent.

Accordingly, the protein of the invention, the holoprotein of the invention and so on can be suitably used for the detection or measurement of calcium ions. Furthermore, the protein of the invention, the holoprotein of the invention, etc. can be used for the assay of transcription activity of promoters, etc. as a reporter protein. Moreover, the holoprotein of the invention, etc. can also be used as detection markers, materials for amusement products, and so on.

The polynucleotide of the invention encodes the protein of the invention described above, and can be used as a reporter gene.

The polynucleotide of the invention, the vector of the invention, the transformant of the invention, etc. can be used to produce the protein of the invention.

The invention claimed is:

1. A polynucleotide comprising a polynucleotide encoding a protein as defined by any one of (a) through (c) below:
    (a) a protein consisting of the amino acid sequence of SEQ ID NO:2;
    (b) a protein comprising the amino acid sequence of SEQ ID NO:2, and having the binding ability to the peroxide of coelenterazine or the peroxide of a coelenterazine derivative to form a holoprotein that emits light by calcium ions; and
    (c) a protein comprising a mutant of the amino acid sequence of SEQ ID NO:2, wherein one to four amino acid(s) are substituted with other amino acid(s) except for the amino acid(s) at positions 107, 110, 120, 140, 179 and 180, and having the binding ability to the peroxide of coelenterazine or the peroxide of a coelenterazine derivative to form a holoprotein that emits light by calcium ions.

2. A recombinant vector comprising the polynucleotide according to claim 1.

3. A transformant having inserted therein the recombinant vector according to claim 2.

4. A method of producing a protein, which comprises culturing a transformant having inserted therein a recombinant vector comprising the polynucleotide of claim 1 and producing the protein as defined by any one of (a) through (c).

5. A kit comprising the polynucleotide of claim 1.

6. A method of detecting or quantifying a calcium ion, which comprises contacting a protein as defined by any one of (a) through (c) below:
    (a) a protein consisting of the amino acid sequence of SEQ ID NO. 2;
    (b) a protein comprising the amino acid sequence of SEQ ID NO: 2, and having the binding ability to the peroxide of coelenterazine or the peroxide of a coelenterazine derivative to form a holoprotein that emits light by calcium ions; and
    (c) a protein comprising a mutant of the amino acid sequence of SEQ ID NO. 2, wherein one to four amino acid(s) are substituted with other amino acid(s) except for the amino acid(s) at positions 107, 110, 120, 140, 179, and 180, and having the binding ability to the peroxide of coelenterazine or the peroxide of a coelenterazine derivative to form a holoprotein that emits light by calcium ions, or a holoprotein comprising the protein and the peroxide of coelenterazine or the peroxide of a coelenterazine derivative,
    with a sample and measuring the luminescence generated to thereby detect or quantify a calcium ion.

7. A method of assaying the activity of a sequence associated with promoter control, which comprises introducing a vector comprising the polynucleotide of claim 1 and the sequence associated with promoter control into a host cell and measuring the luminescence generated by the protein encoded by the polynucleotide to thereby assay the activity of the sequence associated with promoter control.

8. A method of measuring changes in intracellular calcium concentration, which comprises the step of expressing the polynucleotide of claim 1 in a cell to form a photoprotein, and measuring the luminescence generated by the photoprotein to thereby measure changes in intracellular calcium concentration.

9. A method of producing a fluorescent protein, which comprises reacting a protein as defined by any one of (a) through (c) below:
    (a) a protein consisting of the amino acid sequence of SEQ ID NO. 2;
    (b) a protein comprising the amino acid sequence of SEQ ID NO: 2, and having the binding ability to the peroxide of coelenterazine or the peroxide of a coelenterazine derivative to form a holoprotein that emits light by calcium ions; and
    (c) a protein comprising a mutant of the amino acid sequence of SEQ ID NO. 2, wherein one to four amino acid(s) are substituted with other amino acid(s) except for the amino acid(s) at positions 107, 110, 120, 140, 179 and 180, and having the binding ability to the peroxide of coelenterazine or the peroxide of a coelenterazine derivative to form a holoprotein that emits light by calcium ions, with coelenteramide or an analogue thereof in the presence or absence of a calcium ion or a divalent or trivalent ion that can be substituted for the calcium ion.

10. The method according to claim 9, wherein the reaction is carried out in the presence of a reducing agent.

11. The method according to claim 9, wherein the reaction is carried out in the presence of a chelating agent to remove the calcium ion or the divalent or trivalent ion that can be substituted for the calcium ion.

* * * * *

SEQUENCE LISTING

<160> NUMBER OF SEQ ID NOS: 19

<210> SEQ ID NO 1
<211> LENGTH: 570
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(570)

<400> SEQUENCE: 1 gtc aaa ctc aga ccc aac ttc gac aac cca aaa tgg gtc aac aga cac        48

```
Val Lys Leu Arg Pro Asn Phe Asp Asn Pro Lys Trp Val Asn Arg His
1               5                  10                  15 aaa ttt atg ttc aac ttt ttg gac att aac ggc gac gga aaa atc act      96
Lys Phe Met Phe Asn Phe Leu Asp Ile Asn Gly Asp Gly Lys Ile Thr
            20                  25                  30 ttg gat gaa atc gtc tcc aaa gct tcg gat gac att tgc gcc aaa ctt     144
Leu Asp Glu Ile Val Ser Lys Ala Ser Asp Asp Ile Cys Ala Lys Leu
                35                  40                  45 gga gca aca cca gaa cag acc aaa cgt cac cag gat gct gtc gaa gct     192
Gly Ala Thr Pro Glu Gln Thr Lys Arg His Gln Asp Ala Val Glu Ala
        50                  55                  60 ttc ttc aaa aag att ggt atg gat tat ggt aaa gaa gtc gaa ttc cca     240
Phe Phe Lys Lys Ile Gly Met Asp Tyr Gly Lys Glu Val Glu Phe Pro
65                  70                  75                  80 gct ttt gtt gat gga tgg aaa gaa ctg gcc aat tat gac ttg aaa ctt     288
Ala Phe Val Asp Gly Trp Lys Glu Leu Ala Asn Tyr Asp Leu Lys Leu
                    85                  90                  95 tgg tct caa aac aag aaa tct ttg atc cgc gac tgg gga gat gct gtt     336
Trp Ser Gln Asn Lys Lys Ser Leu Ile Arg Asp Trp Gly Asp Ala Val
                100                 105                 110 ttc gac att ttt gac aaa gac gga agt ggc tca atc agt ttg gac gaa     384
Phe Asp Ile Phe Asp Lys Asp Gly Ser Gly Ser Ile Ser Leu Asp Glu
            115                 120                 125 tgg aag gct tat gga cga atc tct gga atc tgc cca tca gac gaa gac     432
Trp Lys Ala Tyr Gly Arg Ile Ser Gly Ile Cys Pro Ser Asp Glu Asp
        130                 135                 140 gcc gaa aag acc ttc aaa cat tgc gat ttg gac aac agt ggc aaa ctt     480
Ala Glu Lys Thr Phe Lys His Cys Asp Leu Asp Asn Ser Gly Lys Leu
145                 150                 155                 160 gat gtt gat gag atg acc aga caa cat ttg gga ttc tgg tac acc ttg     528
Asp Val Asp Glu Met Thr Arg Gln His Leu Gly Phe Trp Tyr Thr Leu
                    165                 170                 175 gac ccc act agt gat ggt ctt tac ggc aat ttt gtt cct taa             570
Asp Pro Thr Ser Asp Gly Leu Tyr Gly Asn Phe Val Pro
                180                 185
```

<210> SEQ ID NO 2
<211> LENGTH: 189
<212> TYPE: PRT
<213> ORGANISM: Artificial sequence
<220> FEATURE:
<223> OTHER INFORMATION: Synthetic Construct

<400> SEQUENCE: 2

```
Val Lys Leu Arg Pro Asn Phe Asp Asn Pro Lys Trp Val Asn Arg His
1               5                  10                  15

Lys Phe Met Phe Asn Phe Leu Asp Ile Asn Gly Asp Gly Lys Ile Thr
            20                  25                  30

Leu Asp Glu Ile Val Ser Lys Ala Ser Asp Asp Ile Cys Ala Lys Leu
        35                  40                  45

Gly Ala Thr Pro Glu Gln Thr Lys Arg His Gln Asp Ala Val Glu Ala
    50                  55                  60

Phe Phe Lys Lys Ile Gly Met Asp Tyr Gly Lys Glu Val Glu Phe Pro
65                  70                  75                  80

Ala Phe Val Asp Gly Trp Lys Glu Leu Ala Asn Tyr Asp Leu Lys Leu
                85                  90                  95

Trp Ser Gln Asn Lys Lys Ser Leu Ile Arg Asp Trp Gly Asp Ala Val
            100                 105                 110

Phe Asp Ile Phe Asp Lys Asp Gly Ser Gly Ser Ile Ser Leu Asp Glu
```

-continued

```
                115                 120                 125
Trp Lys Ala Tyr Gly Arg Ile Ser Gly Ile Cys Pro Ser Asp Glu Asp
    130                 135                 140

Ala Glu Lys Thr Phe Lys His Cys Asp Leu Asp Asn Ser Gly Lys Leu
145                 150                 155                 160

Asp Val Asp Glu Met Thr Arg Gln His Leu Gly Phe Trp Tyr Thr Leu
                165                 170                 175

Asp Pro Thr Ser Asp Gly Leu Tyr Gly Asn Phe Val Pro
                180                 185

<210> SEQ ID NO 3
<211> LENGTH: 657
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(657)

<400> SEQUENCE: 3 atg acc atg att acg cca agc gcg caa tta acc ctc act aaa ggg aac      48
Met Thr Met Ile Thr Pro Ser Ala Gln Leu Thr Leu Thr Lys Gly Asn
1               5                   10                  15 aaa agc tgg agc tcc acc gcg gtg gcg gcc gct cta gaa gtc aaa ctc      96
Lys Ser Trp Ser Ser Thr Ala Val Ala Ala Ala Leu Glu Val Lys Leu
            20                  25                  30 aga ccc aac ttc gac aac cca aaa tgg gtc aac aga cac aaa ttt atg     144
Arg Pro Asn Phe Asp Asn Pro Lys Trp Val Asn Arg His Lys Phe Met
        35                  40                  45 ttc aac ttt ttg gac att aac ggc gac gga aaa atc act ttg gat gaa     192
Phe Asn Phe Leu Asp Ile Asn Gly Asp Gly Lys Ile Thr Leu Asp Glu
    50                  55                  60 atc gtc tcc aaa gct tcg gat gac att tgc gcc aaa ctt gga gca aca     240
Ile Val Ser Lys Ala Ser Asp Asp Ile Cys Ala Lys Leu Gly Ala Thr
65                  70                  75                  80 cca gaa cag acc aaa cgt cac cag gat gct gtc gaa gct ttc ttc aaa     288
Pro Glu Gln Thr Lys Arg His Gln Asp Ala Val Glu Ala Phe Phe Lys
                85                  90                  95 aag att ggt atg gat tat ggt aaa gaa gtc gaa ttc cca gct ttt gtt     336
Lys Ile Gly Met Asp Tyr Gly Lys Glu Val Glu Phe Pro Ala Phe Val
            100                 105                 110 gat gga tgg aaa gaa ctg gcc aat tat gac ttg aaa ctt tgg tct caa     384
Asp Gly Trp Lys Glu Leu Ala Asn Tyr Asp Leu Lys Leu Trp Ser Gln
        115                 120                 125 aac aag aaa tct ttg atc cgc gac tgg gga gat gct gtt ttc gac att     432
Asn Lys Lys Ser Leu Ile Arg Asp Trp Gly Asp Ala Val Phe Asp Ile
    130                 135                 140 ttt gac aaa gac gga agt ggc tca atc agt ttg gac gaa tgg aag gct     480
Phe Asp Lys Asp Gly Ser Gly Ser Ile Ser Leu Asp Glu Trp Lys Ala
145                 150                 155                 160 tat gga cga atc tct gga atc tgc cca tca gac gaa gac gcc gaa aag     528
Tyr Gly Arg Ile Ser Gly Ile Cys Pro Ser Asp Glu Asp Ala Glu Lys
                165                 170                 175 acc ttc aaa cat tgc gat ttg gac aac agt ggc aaa ctt gat gtt gat     576
Thr Phe Lys His Cys Asp Leu Asp Asn Ser Gly Lys Leu Asp Val Asp
            180                 185                 190 gag atg acc aga caa cat ttg gga ttc tgg tac acc ttg gac ccc act     624
Glu Met Thr Arg Gln His Leu Gly Phe Trp Tyr Thr Leu Asp Pro Thr
        195                 200                 205
```

-continued

```
agt gat ggt ctt tac ggc aat ttt gtt cct taa                           657
Ser Asp Gly Leu Tyr Gly Asn Phe Val Pro
    210                 215
```

<210> SEQ ID NO 4
<211> LENGTH: 218
<212> TYPE: PRT
<213> ORGANISM: Artificial sequence
<220> FEATURE:
<223> OTHER INFORMATION: Synthetic Construct

<400> SEQUENCE: 4

```
Met Thr Met Ile Thr Pro Ser Ala Gln Leu Thr Leu Thr Lys Gly Asn
1               5                   10                  15

Lys Ser Trp Ser Ser Thr Ala Val Ala Ala Leu Glu Val Lys Leu
            20                  25                  30

Arg Pro Asn Phe Asp Asn Pro Lys Trp Val Asn Arg His Lys Phe Met
        35                  40                  45

Phe Asn Phe Leu Asp Ile Asn Gly Asp Gly Lys Ile Thr Leu Asp Glu
    50                  55                  60

Ile Val Ser Lys Ala Ser Asp Ile Cys Ala Lys Leu Gly Ala Thr
65                  70                  75                  80

Pro Glu Gln Thr Lys Arg His Gln Asp Ala Val Glu Ala Phe Phe Lys
                85                  90                  95

Lys Ile Gly Met Asp Tyr Gly Lys Glu Val Glu Phe Pro Ala Phe Val
            100                 105                 110

Asp Gly Trp Lys Glu Leu Ala Asn Tyr Asp Leu Lys Leu Trp Ser Gln
        115                 120                 125

Asn Lys Lys Ser Leu Ile Arg Asp Trp Gly Asp Ala Val Phe Asp Ile
    130                 135                 140

Phe Asp Lys Asp Gly Ser Gly Ser Ile Ser Leu Asp Glu Trp Lys Ala
145                 150                 155                 160

Tyr Gly Arg Ile Ser Gly Ile Cys Pro Ser Asp Glu Asp Ala Glu Lys
                165                 170                 175

Thr Phe Lys His Cys Asp Leu Asp Asn Ser Gly Lys Leu Asp Val Asp
            180                 185                 190

Glu Met Thr Arg Gln His Leu Gly Phe Trp Tyr Thr Leu Asp Pro Thr
        195                 200                 205

Ser Asp Gly Leu Tyr Gly Asn Phe Val Pro
    210                 215
```

<210> SEQ ID NO 5
<211> LENGTH: 681
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(681)

<400> SEQUENCE: 5

```
atg aaa aag aca gct atc gcg att gca gtg gca ctg gct ggt ttc gct   48
Met Lys Lys Thr Ala Ile Ala Ile Ala Val Ala Leu Ala Gly Phe Ala
1               5                   10                  15 acc gta gcg cag gcc gcg aat tcc cac cat cac cat cac cat ggt aag   96
Thr Val Ala Gln Ala Ala Asn Ser His His His His His His Gly Lys
            20                  25                  30 ctt cat atg gag ctc gtc aaa ctc aga ccc aac ttc gac aac cca aaa   144
Leu His Met Glu Leu Val Lys Leu Arg Pro Asn Phe Asp Asn Pro Lys
```

```
                35                  40                  45
tgg gtc aac aga cac aaa ttt atg ttc aac ttt ttg gac att aac ggc    192
Trp Val Asn Arg His Lys Phe Met Phe Asn Phe Leu Asp Ile Asn Gly
     50                  55                  60 gac gga aaa atc act ttg gat gaa atc gtc tcc aaa gct tcg gat gac    240
Asp Gly Lys Ile Thr Leu Asp Glu Ile Val Ser Lys Ala Ser Asp Asp
 65                  70                  75                  80 att tgc gcc aaa ctt gga gca aca cca gaa cag acc aaa cgt cac cag    288
Ile Cys Ala Lys Leu Gly Ala Thr Pro Glu Gln Thr Lys Arg His Gln
                 85                  90                  95 gat gct gtc gaa gct ttc ttc aaa aag att ggt atg gat tat ggt aaa    336
Asp Ala Val Glu Ala Phe Phe Lys Lys Ile Gly Met Asp Tyr Gly Lys
            100                 105                 110 gaa gtc gaa ttc cca gct ttt gtt gat gga tgg aaa gaa ctg gcc aat    384
Glu Val Glu Phe Pro Ala Phe Val Asp Gly Trp Lys Glu Leu Ala Asn
        115                 120                 125 tat gac ttg aaa ctt tgg tct caa aac aag aaa tct ttg atc cgc gac    432
Tyr Asp Leu Lys Leu Trp Ser Gln Asn Lys Lys Ser Leu Ile Arg Asp
    130                 135                 140 tgg gga gat gct gtt ttc gac att ttt gac aaa gac gga agt ggc tca    480
Trp Gly Asp Ala Val Phe Asp Ile Phe Asp Lys Asp Gly Ser Gly Ser
145                 150                 155                 160 atc agt ttg gac gaa tgg aag gct tat gga cga atc tct gga atc tgc    528
Ile Ser Leu Asp Glu Trp Lys Ala Tyr Gly Arg Ile Ser Gly Ile Cys
                165                 170                 175 cca tca gac gaa gac gcc gaa aag acc ttc aaa cat tgc gat ttg gac    576
Pro Ser Asp Glu Asp Ala Glu Lys Thr Phe Lys His Cys Asp Leu Asp
            180                 185                 190 aac agt ggc aaa ctt gat gtt gat gag atg acc aga caa cat ttg gga    624
Asn Ser Gly Lys Leu Asp Val Asp Glu Met Thr Arg Gln His Leu Gly
        195                 200                 205 ttc tgg tac acc ttg gac ccc act agt gat ggt ctt tac ggc aat ttt    672
Phe Trp Tyr Thr Leu Asp Pro Thr Ser Asp Gly Leu Tyr Gly Asn Phe
    210                 215                 220 gtt cct taa                                                        681
Val Pro
225

<210> SEQ ID NO 6
<211> LENGTH: 226
<212> TYPE: PRT
<213> ORGANISM: Artificial sequence
<220> FEATURE:
<223> OTHER INFORMATION: Synthetic Construct

<400> SEQUENCE: 6

Met Lys Lys Thr Ala Ile Ala Ile Ala Val Ala Leu Ala Gly Phe Ala
 1               5                  10                  15

Thr Val Ala Gln Ala Ala Asn Ser His His His His His Gly Lys
            20                  25                  30

Leu His Met Glu Leu Val Lys Leu Arg Pro Asn Phe Asp Asn Pro Lys
        35                  40                  45

Trp Val Asn Arg His Lys Phe Met Phe Asn Phe Leu Asp Ile Asn Gly
     50                  55                  60

Asp Gly Lys Ile Thr Leu Asp Glu Ile Val Ser Lys Ala Ser Asp Asp
 65                  70                  75                  80

Ile Cys Ala Lys Leu Gly Ala Thr Pro Glu Gln Thr Lys Arg His Gln
                 85                  90                  95

Asp Ala Val Glu Ala Phe Phe Lys Lys Ile Gly Met Asp Tyr Gly Lys
```

```
            100                 105                 110
Glu Val Glu Phe Pro Ala Phe Val Asp Gly Trp Lys Glu Leu Ala Asn
        115                 120                 125

Tyr Asp Leu Lys Leu Trp Ser Gln Asn Lys Lys Ser Leu Ile Arg Asp
        130                 135                 140

Trp Gly Asp Ala Val Phe Asp Ile Phe Asp Lys Asp Gly Ser Gly Ser
145                 150                 155                 160

Ile Ser Leu Asp Glu Trp Lys Ala Tyr Gly Arg Ile Ser Gly Ile Cys
        165                 170                 175

Pro Ser Asp Glu Asp Ala Glu Lys Thr Phe Lys His Cys Asp Leu Asp
        180                 185                 190

Asn Ser Gly Lys Leu Asp Val Asp Glu Met Thr Arg Gln His Leu Gly
        195                 200                 205

Phe Trp Tyr Thr Leu Asp Pro Thr Ser Asp Gly Leu Tyr Gly Asn Phe
        210                 215                 220

Val Pro
225

<210> SEQ ID NO 7
<211> LENGTH: 31
<212> TYPE: DNA
<213> ORGANISM: Artificial sequence
<220> FEATURE:
<223> OTHER INFORMATION: synthetic DNA

<400> SEQUENCE: 7
cggtctagaa gtcaaactca gacccaactt c                              31

<210> SEQ ID NO 8
<211> LENGTH: 21
<212> TYPE: DNA
<213> ORGANISM: Artificial sequence
<220> FEATURE:
<223> OTHER INFORMATION: synthetic DNA

<400> SEQUENCE: 8
gtctgatggg cagattccag a                                         21

<210> SEQ ID NO 9
<211> LENGTH: 21
<212> TYPE: DNA
<213> ORGANISM: Artificial sequence
<220> FEATURE:
<223> OTHER INFORMATION: synthetic DNA

<400> SEQUENCE: 9
atctgcccat cagacgaaga c                                         21

<210> SEQ ID NO 10
<211> LENGTH: 30
<212> TYPE: DNA
<213> ORGANISM: Artificial sequence
<220> FEATURE:
<223> OTHER INFORMATION: synthetic DNA

<400> SEQUENCE: 10
ggcgtcgact taaggaacaa aattgccgta                                30

<210> SEQ ID NO 11
<211> LENGTH: 21
<212> TYPE: DNA
<213> ORGANISM: Artificial sequence
```

-continued

```
<220> FEATURE:
<223> OTHER INFORMATION: synthetic DNA

<400> SEQUENCE: 11
aacagcatct ccccagtcgc g                                              21

<210> SEQ ID NO 12
<211> LENGTH: 21
<212> TYPE: DNA
<213> ORGANISM: Artificial sequence
<220> FEATURE:
<223> OTHER INFORMATION: synthetic DNA

<400> SEQUENCE: 12
tggggagatg ctgttttcga c                                              21

<210> SEQ ID NO 13
<211> LENGTH: 48
<212> TYPE: DNA
<213> ORGANISM: Artificial sequence
<220> FEATURE:
<223> OTHER INFORMATION: synthetic DNA

<400> SEQUENCE: 13
ggcgtcgact taaggaacaa aattgccgta aagaccatca ctagtggg                 48

<210> SEQ ID NO 14
<211> LENGTH: 27
<212> TYPE: DNA
<213> ORGANISM: Artificial sequence
<220> FEATURE:
<223> OTHER INFORMATION: synthetic DNA

<400> SEQUENCE: 14
ggcgagctca gacccaactt cgacaac                                        27

<210> SEQ ID NO 15
<211> LENGTH: 30
<212> TYPE: DNA
<213> ORGANISM: Artificial sequence
<220> FEATURE:
<223> OTHER INFORMATION: synthetic DNA

<400> SEQUENCE: 15
cggctcgagt taaggaacaa aattgccgta                                     30

<210> SEQ ID NO 16
<211> LENGTH: 597
<212> TYPE: DNA
<213> ORGANISM: Clytia gregaria
<220> FEATURE:
<221> NAME/KEY: CDS
<222> LOCATION: (1)..(597)

<400> SEQUENCE: 16 atg gct gac act gca tca aaa tac gcc gtc aaa ctc aga ccc aac ttc     48
Met Ala Asp Thr Ala Ser Lys Tyr Ala Val Lys Leu Arg Pro Asn Phe
1               5                   10                  15 gac aac cca aaa tgg gtc aac aga cac aaa ttt atg ttc aac ttt ttg     96
Asp Asn Pro Lys Trp Val Asn Arg His Lys Phe Met Phe Asn Phe Leu
            20                  25                  30 gac att aac ggc gac gga aaa atc act ttg gat gaa atc gtc tcc aaa    144
Asp Ile Asn Gly Asp Gly Lys Ile Thr Leu Asp Glu Ile Val Ser Lys
        35                  40                  45 gct tcg gat gac att tgc gcc aaa ctt gga gca aca cca gaa cag acc    192
```

```
                Ala Ser Asp Asp Ile Cys Ala Lys Leu Gly Ala Thr Pro Glu Gln Thr
                    50                  55                  60 aaa cgt cac cag gat gct gtc gaa gct ttc ttc aaa aag att ggt atg          240
Lys Arg His Gln Asp Ala Val Glu Ala Phe Phe Lys Lys Ile Gly Met
65                  70                  75                  80 gat tat ggt aaa gaa gtc gaa ttc cca gct ttt gtt gat gga tgg aaa          288
Asp Tyr Gly Lys Glu Val Glu Phe Pro Ala Phe Val Asp Gly Trp Lys
                85                  90                  95 gaa ctg gcc aat tat gac ttg aaa ctt tgg tct caa aac aag aaa tct          336
Glu Leu Ala Asn Tyr Asp Leu Lys Leu Trp Ser Gln Asn Lys Lys Ser
            100                 105                 110 ttg atc cgc gac tgg gga gaa gct gtt ttc gac att ttt gac aaa gac          384
Leu Ile Arg Asp Trp Gly Glu Ala Val Phe Asp Ile Phe Asp Lys Asp
        115                 120                 125 gga agt ggc tca atc agt ttg gac gaa tgg aag gct tat gga cga atc          432
Gly Ser Gly Ser Ile Ser Leu Asp Glu Trp Lys Ala Tyr Gly Arg Ile
130                 135                 140 tct gga atc tgc tca tca gac gaa gac gcc gaa aag acc ttc aaa cat          480
Ser Gly Ile Cys Ser Ser Asp Glu Asp Ala Glu Lys Thr Phe Lys His
145                 150                 155                 160 tgc gat ttg gac aac agt ggc aaa ctt gat gtt gat gag atg acc aga          528
Cys Asp Leu Asp Asn Ser Gly Lys Leu Asp Val Asp Glu Met Thr Arg
                165                 170                 175 caa cat ttg gga ttc tgg tac acc ttg gac ccc aac gct gat ggt ctt          576
Gln His Leu Gly Phe Trp Tyr Thr Leu Asp Pro Asn Ala Asp Gly Leu
            180                 185                 190 tac ggc aat ttt gtt cct taa                                              597
Tyr Gly Asn Phe Val Pro
        195

<210> SEQ ID NO 17
<211> LENGTH: 198
<212> TYPE: PRT
<213> ORGANISM: Clytia gregaria

<400> SEQUENCE: 17

Met Ala Asp Thr Ala Ser Lys Tyr Ala Val Lys Leu Arg Pro Asn Phe
1               5                   10                  15

Asp Asn Pro Lys Trp Val Asn Arg His Lys Phe Met Phe Asn Phe Leu
                20                  25                  30

Asp Ile Asn Gly Asp Gly Lys Ile Thr Leu Asp Glu Ile Val Ser Lys
            35                  40                  45

Ala Ser Asp Asp Ile Cys Ala Lys Leu Gly Ala Thr Pro Glu Gln Thr
        50                  55                  60

Lys Arg His Gln Asp Ala Val Glu Ala Phe Phe Lys Lys Ile Gly Met
65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
        115                 120                 125

Gly Ser Gly Ser Ile Ser Leu Asp Glu Trp Lys Ala Tyr Gly Arg Ile
130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175
```

```
Gln His Leu Gly Phe Trp Tyr Thr Leu Asp Pro Asn Ala Asp Gly Leu
            180                 185                 190

Tyr Gly Asn Phe Val Pro
        195

<210> SEQ ID NO 18
<211> LENGTH: 570
<212> TYPE: DNA
<213> ORGANISM: Clytia gregaria
<220> FEATURE:
<221> NAME/KEY: CDS
<222> LOCATION: (1)..(570)

<400> SEQUENCE: 18 gtc aaa ctc aga ccc aac ttc gac aac cca aaa tgg gtc aac aga cac      48
Val Lys Leu Arg Pro Asn Phe Asp Asn Pro Lys Trp Val Asn Arg His
1               5                   10                  15 aaa ttt atg ttc aac ttt ttg gac att aac ggc gac gga aaa atc act      96
Lys Phe Met Phe Asn Phe Leu Asp Ile Asn Gly Asp Gly Lys Ile Thr
            20                  25                  30 ttg gat gaa atc gtc tcc aaa gct tcg gat gac att tgc gcc aaa ctt     144
Leu Asp Glu Ile Val Ser Lys Ala Ser Asp Asp Ile Cys Ala Lys Leu
        35                  40                  45 gga gca aca cca gaa cag acc aaa cgt cac cag gat gct gtc gaa gct     192
Gly Ala Thr Pro Glu Gln Thr Lys Arg His Gln Asp Ala Val Glu Ala
    50                  55                  60 ttc ttc aaa aag att ggt atg gat tat ggt aaa gaa gtc gaa ttc cca     240
Phe Phe Lys Lys Ile Gly Met Asp Tyr Gly Lys Glu Val Glu Phe Pro
65                  70                  75                  80 gct ttt gtt gat gga tgg aaa gaa ctg gcc aat tat gac ttg aaa ctt     288
Ala Phe Val Asp Gly Trp Lys Glu Leu Ala Asn Tyr Asp Leu Lys Leu
                85                  90                  95 tgg tct caa aac aag aaa tct ttg atc cgc gac tgg gga gaa gct gtt     336
Trp Ser Gln Asn Lys Lys Ser Leu Ile Arg Asp Trp Gly Glu Ala Val
            100                 105                 110 ttc gac att ttt gac aaa gac gga agt ggc tca atc agt ttg gac gaa     384
Phe Asp Ile Phe Asp Lys Asp Gly Ser Gly Ser Ile Ser Leu Asp Glu
        115                 120                 125 tgg aag gct tat gga cga atc tct gga atc tgc tca tca gac gaa gac     432
Trp Lys Ala Tyr Gly Arg Ile Ser Gly Ile Cys Ser Ser Asp Glu Asp
    130                 135                 140 gcc gaa aag acc ttc aaa cat tgc gat ttg gac aac agt ggc aaa ctt     480
Ala Glu Lys Thr Phe Lys His Cys Asp Leu Asp Asn Ser Gly Lys Leu
145                 150                 155                 160 gat gtt gat gag atg acc aga caa cat ttg gga ttc tgg tac acc ttg     528
Asp Val Asp Glu Met Thr Arg Gln His Leu Gly Phe Trp Tyr Thr Leu
                165                 170                 175 gac ccc aac gct gat ggt ctt tac ggc aat ttt gtt cct taa             570
Asp Pro Asn Ala Asp Gly Leu Tyr Gly Asn Phe Val Pro
            180                 185

<210> SEQ ID NO 19
<211> LENGTH: 189
<212> TYPE: PRT
<213> ORGANISM: Clytia gregaria

<400> SEQUENCE: 19

Val Lys Leu Arg Pro Asn Phe Asp Asn Pro Lys Trp Val Asn Arg His
1               5                   10                  15

Lys Phe Met Phe Asn Phe Leu Asp Ile Asn Gly Asp Gly Lys Ile Thr
            20                  25                  30
```

```
Leu Asp Glu Ile Val Ser Lys Ala Ser Asp Asp Ile Cys Ala Lys Leu
        35                  40                  45
Gly Ala Thr Pro Glu Gln Thr Lys Arg His Gln Asp Ala Val Glu Ala
 50                  55                  60
Phe Phe Lys Lys Ile Gly Met Asp Tyr Gly Lys Glu Val Glu Phe Pro
 65              70                  75                  80
Ala Phe Val Asp Gly Trp Lys Glu Leu Ala Asn Tyr Asp Leu Lys Leu
            85                  90                  95
Trp Ser Gln Asn Lys Lys Ser Leu Ile Arg Asp Trp Gly Glu Ala Val
            100             105             110
Phe Asp Ile Phe Asp Lys Asp Gly Ser Gly Ser Ile Ser Leu Asp Glu
        115             120             125
Trp Lys Ala Tyr Gly Arg Ile Ser Gly Ile Cys Ser Ser Asp Glu Asp
    130             135             140
Ala Glu Lys Thr Phe Lys His Cys Asp Leu Asp Asn Ser Gly Lys Leu
145             150             155             160
Asp Val Asp Glu Met Thr Arg Gln His Leu Gly Phe Trp Tyr Thr Leu
                165             170             175
Asp Pro Asn Ala Asp Gly Leu Tyr Gly Asn Phe Val Pro
            180             185
```